(12) United States Patent
Beinhocker

(10) Patent No.: US 7,332,728 B2
(45) Date of Patent: Feb. 19, 2008

(54) TAMPER-PROOF CONTAINER

(75) Inventor: Gilbert D. Beinhocker, Belmont, MA (US)

(73) Assignee: Tamperproof Container Licensing Corp., Belmont, MA (US)

( * ) Notice: Subject to any disclaimer, the term of this patent is extended or adjusted under 35 U.S.C. 154(b) by 13 days.

(21) Appl. No.: 11/444,160

(22) Filed: May 31, 2006

(65) Prior Publication Data

US 2006/0249664 A1 Nov. 9, 2006

Related U.S. Application Data

(63) Continuation-in-part of application No. 10/981,836, filed on Nov. 5, 2004, now Pat. No. 7,211,783.

(60) Provisional application No. 60/706,501, filed on Aug. 8, 2005, provisional application No. 60/687,409, filed on Jun. 3, 2005.

(51) Int. Cl.
*G01T 1/00* (2006.01)
(52) U.S. Cl. .................................. 250/474.1
(58) Field of Classification Search ............. 250/474.1
See application file for complete search history.

(56) References Cited

U.S. PATENT DOCUMENTS

| 2,311,613 | A | 2/1943 | Slayter |
| 3,320,114 | A | 5/1967 | Schulz |
| 3,634,845 | A | 1/1972 | Colman ..................... 340/274 |
| 3,714,644 | A | 1/1973 | Hellstrom .................. 340/274 |
| 3,947,837 | A | 3/1976 | Bitterice .................... 340/274 |
| 4,095,872 | A | 6/1978 | Stieff et al. .............. 350/96.24 |
| 4,118,211 | A | 10/1978 | Au Coin et al. |
| 4,161,348 | A | 7/1979 | Ulrich ....................... 350/96.2 |

(Continued)

FOREIGN PATENT DOCUMENTS

WO  WO 9311513 A1 *  6/1993

OTHER PUBLICATIONS

Giallorenzi et al. Optical fiber sensor technology, IEEE Journal of Quantum Electronics, vol. QE-18, No. 4 (Apr. 1982), pp. 626-665.*

(Continued)

*Primary Examiner*—David Porta
*Assistant Examiner*—Shun Lee
(74) *Attorney, Agent, or Firm*—Weingarten, Schurgin, Gagnebin & Lebovici LLP

(57) ABSTRACT

A system and method for detecting radiation from a source in a container is disclosed. A continuous optical fiber path is disposed in a medium which is part of or associated with a container and which encloses the volumetric space of the container. The optical fiber path provides a volumetric mass of optical fiber which is reactive to radiation from a radiation source in the container to cause an irreversible change in the light carrying capacity or other characteristic of the optical fiber. A light source is coupled to one end of the optical fiber path for introducing light having a predetermined characteristic. A light detector is coupled to the other end of the optical path for receiving light from the optical path. A circuit is coupled to the light detector and is operative to detect a change in the predetermined characteristic of the light and to provide an indication thereof.

17 Claims, 19 Drawing Sheets

U.S. PATENT DOCUMENTS

| | | | | |
|---|---|---|---|---|
| 4,175,827 | A | 11/1979 | McMahon | 350/96.14 |
| 4,195,907 | A | 4/1980 | Zamja et al. | 350/96.32 |
| 4,217,488 | A | 8/1980 | Hubbard | 455/612 |
| 4,228,425 | A | 10/1980 | Cooke | 340/550 |
| 4,234,875 | A | 11/1980 | Williams | 340/550 |
| 4,297,684 | A | 10/1981 | Butter | 340/557 |
| 4,367,460 | A | 1/1983 | Hodara | 340/550 |
| 4,447,123 | A | 5/1984 | Page et al. | 350/96.24 |
| 4,488,269 | A * | 12/1984 | Robinson et al. | 136/213 |
| 4,538,527 | A | 9/1985 | Kitchen | 109/21 |
| 4,573,202 | A | 2/1986 | Lee | |
| 4,603,252 | A | 7/1986 | Malek et al. | 250/227 |
| 4,772,092 | A | 9/1988 | Hofer et al. | 350/96.24 |
| 4,801,213 | A | 1/1989 | Frey et al. | |
| 4,867,820 | A | 9/1989 | Jacobson et al. | 156/101 |
| 4,931,771 | A | 6/1990 | Kahn | 340/556 |
| 4,935,723 | A | 6/1990 | Vallance | 340/550 |
| 4,972,176 | A | 11/1990 | Vallance | 340/550 |
| 5,049,855 | A | 9/1991 | Slemon et al. | 340/550 |
| 5,180,060 | A | 1/1993 | Forti et al. | |
| 5,194,847 | A | 3/1993 | Taylor et al. | 340/557 |
| 5,309,533 | A | 5/1994 | Bonniau et al. | 385/11 |
| 5,355,208 | A | 10/1994 | Crawford et al. | 356/35.5 |
| 5,359,416 | A | 10/1994 | Mueller | 356/371 |
| 5,568,124 | A | 10/1996 | Joyce et al. | 340/550 |
| 5,592,149 | A | 1/1997 | Alizi | 340/550 |
| 5,609,952 | A * | 3/1997 | Weiss | 428/298.1 |
| 5,769,232 | A | 6/1998 | Cash et al. | |
| 5,790,025 | A | 8/1998 | Amer et al. | 340/571 |
| 6,002,501 | A | 12/1999 | Smith et al. | 359/110 |
| 6,065,870 | A | 5/2000 | Nunez | |
| 6,213,167 | B1 | 4/2001 | Greenland | |
| 6,556,138 | B1 | 4/2003 | Sliva et al. | 340/568.1 |
| 7,098,444 | B2 * | 8/2006 | Beinhocker | 250/227.14 |
| 7,211,783 | B2 * | 5/2007 | Beinhocker | 250/227.14 |
| 2002/0089434 | A1 | 7/2002 | Ghazarian | 340/988 |
| 2003/0151509 | A1 | 8/2003 | Iannotti et al. | 340/541 |
| 2003/0174059 | A1 | 9/2003 | Reeves | 340/573.4 |
| 2003/0193032 | A1 | 10/2003 | Marshall | 250/474.1 |
| 2004/0037091 | A1 | 2/2004 | Guy | 362/582 |
| 2004/0046660 | A1 * | 3/2004 | Ando | 340/545.6 |
| 2004/0047142 | A1 | 3/2004 | Goslee | 362/84 |
| 2004/0056767 | A1 | 3/2004 | Porter | 340/541 |

OTHER PUBLICATIONS

Bonner, Robert C., "Remarks of U.S. Customs Commissioner Robert C. Bonner; U.S. Customs and Border Protection C-TPAT Conference San Francisco, California Oct. 30, 2003," http://www.cpb.gov/xp/cgov/newsroom/commissioner/speeches_statements/Oct30,2003.xml (8 pages).

Brichard et al., "Gamma dose rate effect in erbium-doped fibers for space gyroscopes" IEEE, 3 pages.

Kimura et al., "New Techniques to Apply Optical Fiber Image Guide to Nuclear Facilities," J. Nuc. Sci. and Tech., vol. 39, No. 6, pp. 603-607 (Jun. 2002).

Lu et al., "Gamma-induced attenuation in normal single-mode and multimode, Ge-doped and P-doped optical fibers: A fiber optic dosimeter for low dose levels," Published on the NRC Research Press Web site on May 11, 2000, Can. J. Phys. vol. 78, pp. 89-97.

Nucsafe Inc., Introduction "Fiber Sensing Technology—The Long and Short of It," http://nucsafe.com/Puma/introduction.htm May 21, 2004, p. 1 of 1.

Nucsafe Inc., "Why Neutrons," http://nucsafe.com/Puma/why_neutrons.htm, May 21, 2004, p. 1 of 1.

Nucsafe Inc., "Guardian CRMS," http://nucsafe.com/Puma/guardian_crms.htm, pgs. May 21, 2004, 6 pages.

Nucsafe Inc., "Fiber Facility," http://nucsafe.com/Puma/fiber_facilities.htm, May 21, 2004, 2 pages.

Nucsafe Inc., "Detecting Neutrons," http://nucsafe.com/Puma/detecting_neutrons.htm, May 21, 2004, 3 pages.

Nucsafe Inc., "Photonics," http://nucsafe.com/Puma/pr_photonicsspectra.htm, Jul. 9, 2004, 2 pages.

Nucsafe Inc., "Tech Transfer," http://nucsafe.com/Puma/pr_techtransfer.htm, Jul. 9, 2004, 2 pages.

Nucsafe Inc., "Press Release—Frist Applauds Job Creation at Oak Ridge Based-Nucsafe," http://nucsafe.com/Puma/pr_knoxnews.htm, Jul. 9, 2004, 3 pages.

Nucsafe Inc., "Optical Properties," http://nucsafe.com/Puma/properties_of_scintillating_fibe.htm, Jan. 12, 2005, p. 1 of 1.

Ott, Melanie N., "Radiation Effects Data on Commercially Available Optical Fiber: Database Summary," Nuclear Science and Radiation Effects Conference, Phoenix, Arizona, NSREC 2002, Data Workshop Proceedings, July, 8 pages (we believe this to be accurate).

Ott, Melanie N., "Radiation Effects Expected for Fiber Laser/Amplifier Rare Earth Doped Optical Fiber," NASA Survey Report (Mar. 26, 2004), 7 pages.

* cited by examiner

TAMPER-PROOF CONTAINER

CROSS-REFERENCE TO RELATED APPLICATIONS

This application is a continuation-in-part of U.S. patent application Ser. No. 10/981,836 filed Nov. 5, 2004, now U.S. Pat. No. 7,211,783 titled "Tamper Proof Container". This application claims the benefit of U.S. Provisional Application No. 60/706,501, titled "Tamper Proof Container," filed Aug. 8, 2005 and U.S. Provisional Application No. 60/687,409, titled "Tamper Proof Container," filed Jun. 3, 2005.

This application is related to U.S. patent application Ser. No. 11/027,059, titled "Tamper Proof Container," filed Dec. 30, 2004, now U.S. Pat. No. 6,995,353, U.S. patent application Ser. No. 11/349,049, titled "Tamper Proof Container," filed Feb. 7, 2006, and U.S. patent application Ser. No. 10/837,883, titled "Tamper Proof Container," filed May 3, 2004.

STATEMENT REGARDING FEDERALLY SPONSORED RESEARCH OR DEVELOPMENT (Not Applicable)

BACKGROUND OF THE INVENTION

1. Field of the Invention

The present invention relates to security systems for shipping containers, boxes, cartons and the like and, more particularly, to such security systems that can detect tampering with, or breaches in, surfaces of such containers or nuclear radiation from materials placed in the containers.

2. Description of the Prior Art

Cargo is often shipped in standardized containers, such as those used on trucks, trains, ships and aircraft. Smaller units of cargo are typically shipped in cardboard boxes and the like. It is often difficult or impossible to adequately guard these containers and boxes while they are in transit, such as on the high seas. In addition, some shipments originate in countries where port or rail yard security may not be adequate. Consequently, these containers and boxes are subject to tampering by thieves, smugglers, terrorists, and other unscrupulous people. A breached container can, for example, be looted or surreptitiously loaded with contraband, such as illegal drugs, weapons, explosives, contaminants or a weapon of mass destruction, such as a nuclear weapon or a radiological weapon, with catastrophic results. Alternatively, a nuclear or radiological weapon can be loaded by a rogue state or terrorist organization into such a container for shipment without necessarily breaching the container.

Such breaches and weapons are difficult to detect. The sheer number of containers and boxes being shipped every day makes it difficult to adequately inspect each one. Even a visual inspection of the exterior of a container is unlikely to reveal a breach. Shipping containers are subject to rough handling by cranes and other heavy equipment. Many of them have been damaged multiple times in the natural course of business and subsequently patched to extend their useful lives. Thus, upon inspection, a surreptitiously breached and patched container is likely to appear unremarkable. Furthermore, many security professionals would prefer to detect breached containers and radioactive cargoes prior to the containers entering a port and possibly preventing such containers from ever entering the port. The current method of placing a seal across the locking mechanism of a container door is of limited value, whether there is a physical breach of the container or not, because the nuclear or radiological weapon could be loaded by terrorist as legitimate cargo. For example, the terrorists could circumvent or corrupt inventory controls and cargo manifest delivery systems using unscrupulous confederates. A single breach or circumvention of a cargo delivery system by whatever means can have catastrophic consequences.

It is known that optical fibers used for communication systems and the like can be sensitive to radiation in terms of adversely affecting the qualitative and quantitative transmission of light in the optical fiber. Such fibers are usually designed or selected to minimize the sensitivity of the fiber to impinging radiation, a process called "hardening". Such fibers are also often designed or selected to recover from radiation induced darkening so that the fibers can remain useable for the intended purpose of transmitting light signals. Radiation dosimeters are also known for detecting nuclear radiation and such dosimeters are usually recyclable and reusable by recovering from the affects of received radiation.

BRIEF SUMMARY OF THE INVENTION

Embodiments of the present invention can detect a physical breach of the interior surface of a shipping container or box or radiation from a radioactive source within or near the container or box, and can then trigger an alarm or notify a central monitoring location, such as a ship's control room or a port notification system. At least one liner sheet lines at least a portion of at least one interior surface of the shipping container or box, such that a physical breach of the portion of the interior surface also damages the liner sheet, or radiation from a radioactive source, such as a nuclear or radiological weapon, impinges on the liner sheet. It is a well known physics phenomenon that radiation will directly affect the atomic and molecular structures of crystals forming the glass or silica in optical fibers by creating irregularities in crystalline structure called "color centers". The liner sheet defines an optical path extending across at least a portion of the sheet. The optical path is monitored for a change in electromagnetic radiation intensity, such as a loss or reduction of continuity of light transmission signal; or other optical characteristic of the optical path, or a change in a characteristic of the light signal, such as a frequency or phase shift. If the container or box interior surface is breached or the optical path is irradiated, one or more portions of the optical path are affected and the optical path is broken or altered.

For example, a breach of the container or box can break the optical path by cutting the core of the optical fiber which is typically 10 to 100 microns in diameter. The destruction of the core, causes an instantaneous and complete loss of light transmission. Thus the optical fiber acts as a true binary switch, it is either on or off; light conducting or non-conducting. This "binary switch" is in effect passing a single binary bit of information around the single continuous light path i.e. light signal is present or it is not present. The system is in effect "an optical fuse", and analagous to an electrical fuse i.e. conducting of non-conducting. Alternatively, radiation can reduce or alter the light transmissibility of the optical path. The detected change in the optical path can be used to trigger an alarm, such as an annunciator or cause an electronic notification signal to be sent to a monitoring station via any of a wide variety of existing telecommunications networks, such as the Internet and/or a wireless telecommunications network. In addition, a detailed accompanying message can provide information about the nature of the breach, time, location, cargo manifest, etc.

In one aspect of the invention used to detect radiation, an optical fiber is employed which irreversibility responds to received radiation such that the fiber cannot self anneal or otherwise recover its light transmission characteristics after being subject to radiation. Thus the system employing such a fiber provides a true single onetime use continuous monitoring system. The system can be likened to an electrical fuse which when blown in the presence of excessive electrical current cannot be reused or recover from the over current condition. According to the present invention disruption in the transmission of a light beam in the single continuous optical circuit provided by the optical fiber causes an alarm signal which can, for example, be sent to a designated monitoring station in response to radiation darkening of the optical fiber circuit.

Radiation of various types, such as: Gamma, X-Ray, Beta, Alpha and Neutron particles can reduce, alter, or interrupt the transmission of many types of light that may be used to produce a light signal transmission in an optical fiber path. In order to enhance the detection of incident radiation within a cargo container on the optical fiber path inside of the container, the light introduced into the optical fiber can have a predetermined characteristic which is detectable at the receiving end of the fiber. In one embodiment a coded sequence of light pulses is transmitted along the optical fiber path, and change in the pulses or data derived from the pulses over time can be detected as an indication of radiation incident on the fiber. Alternatively, light pulses can provide binary bit patterns which are transmitted through the optical fiber and a detected predetermined error rate employed as an indication of radiation detection caused by a specific radioactive material. The error rate can increase as the optical transmissibility of the fiber decreases due to exposure to radiation which causes a darkening of the optical fiber. This increase in error rate can provide an indication of detected radiation both as to decay time (half-life) and quantity of radioactive material present. A mathematical profile of the error rate over time can be correlated to known decay profiles of various nuclear isotopes to identify particular isotopes producing radiation that impinges on the fiber. Changes in the polarization of light transmitted by the fiber can also be employed for radiation detection in accordance with aspects of the invention. Changes in the relative speed of two orthogonally polarized components of light transmitted by an optical fiber can also be employed as a measure of radiation reception.

A system and method according to the invention can be embodied in a variety of ways suitable for particular enclosures, containers, boxes, cartons and the like. A continuous optical fiber path is disposed in a medium which is part of or associated with a container and which encloses the volumetric space of the container. The optical fiber path provides a volumetric mass of optical fiber which is reactive to radiation from a radiation source in the container to cause an irreversible change in the light carrying capacity or other characteristic of the optical fiber. A light source is coupled to one end of the optical fiber path for introducing light having a predetermined characteristic. A light detector is coupled to the other end of the optical path for receiving light from the optical path. A circuit is coupled to the light detector and is operative to detect a change in the predetermined characteristic of the light and to provide an indication thereof.

BRIEF DESCRIPTION OF THE SEVERAL VIEWS OF THE DRAWINGS

These and other features, advantages, aspects and embodiments of the present invention will become more apparent to those skilled in the art from the following detailed description of embodiments of the present invention when taken with reference to the accompanying drawings, in which the first digit of each reference numeral identifies the figure in which the corresponding item is first introduced and in which.

DETAILED DESCRIPTION OF THE INVENTION

The contents of the U.S. patent applications identified above are all hereby incorporated by reference herein.

The present invention provides methods and apparatus to detect tampering with a six-sided or other type of container or box or other surface or a source of radiation within or near the container, box or surface, as well as methods of manufacturing such apparatus. A preferred embodiment detects a breach in a monitored surface of a container, box or fence or radiation from a source. A liner sheet lines at least a portion of an interior surface of the container, box or fence, such that a breach of the portion of the container interior surface or fence damages the liner sheet or radiation from the source impinges on at least a portion of the liner sheet. The liner sheet defines an optical path extending across at least a portion of the sheet. For example, an optical fiber can be woven into, or sandwiched between layers of, the liner sheet. The optical path is monitored for a change in an optical characteristic of the optical path. For example, a light source can illuminate one end of the optical fiber, and a light sensor can be used to detect the illumination, or a change therein, at the other end of the optical fiber. If the container, box or fence surface is breached, one or more portions of the optical fiber are severed or otherwise damaged, and the optical path is broken or altered. If radiation, such as gamma rays, irradiates all or a portion of the optical fiber, the transmissibility of irradiated portion(s) of the optical fiber changes, and the optical path is altered. The detected change in the optical path can be used to trigger an alarm, such as an annunciator. In addition, a message can be sent, such as by a wireless communication system and/or the Internet, to a central location, such as a ship's control room or a port notification system. In some embodiments, as little as a single nick, cut, pinch, bend, compression, stretch, twist or other damage to the optical fiber can be detected, thus a change in the light transmissibility characteristic of a single optical fiber can protect the entire volume of the container or box.

Figure 1:
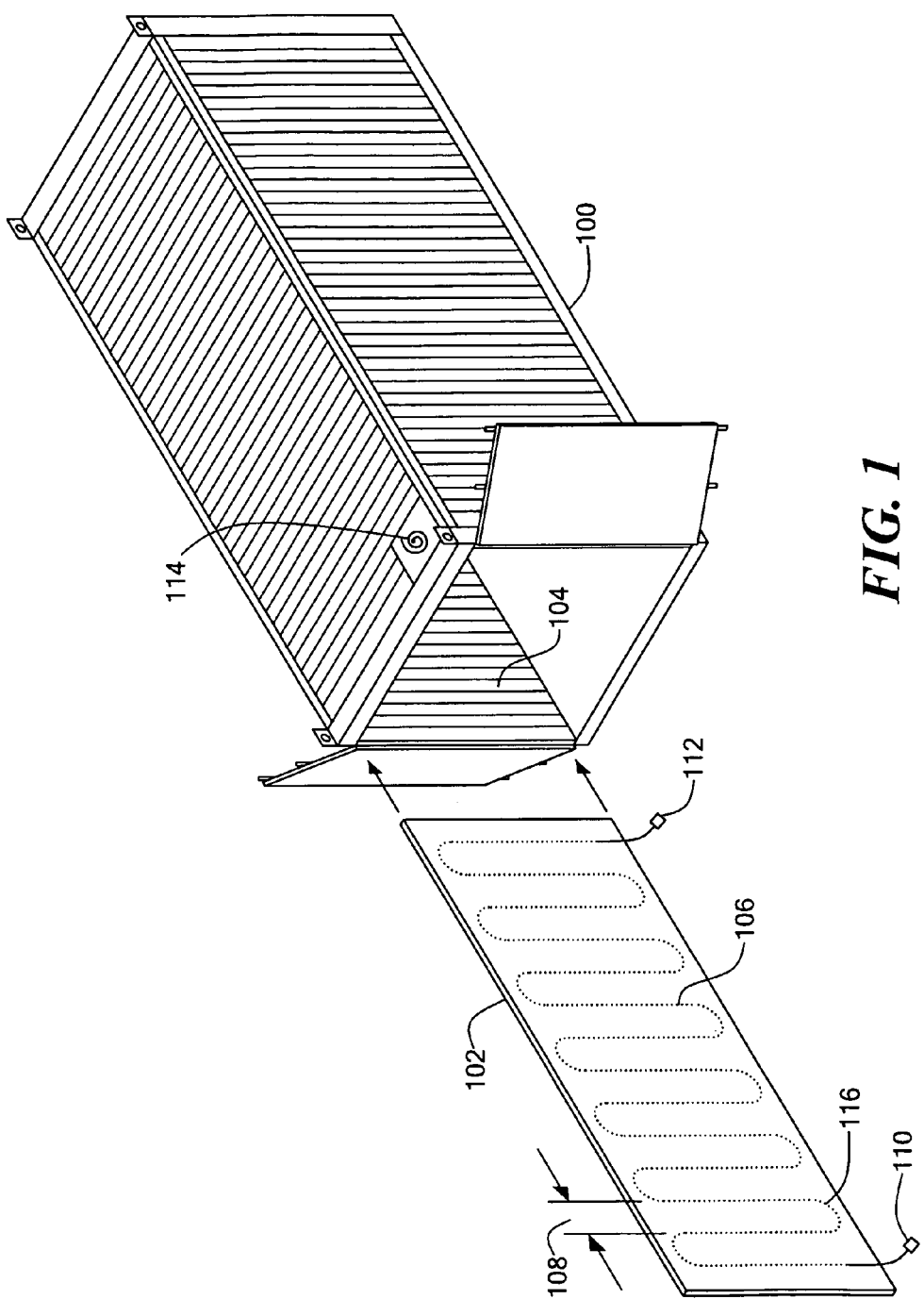
FIG. 1 is a perspective view of a liner sheet, according to one embodiment of the present invention, being inserted into a shipping container.

Embodiments of the present invention can be used in containers typically used to transport cargo by truck, railroad, ship or aircraft. FIG. 1 illustrates an embodiment of the present invention being inserted into one such container 100. In this example, the container 100 is an ISO standard container, but other types of containers or boxes can be used. The embodiment illustrated in FIG. 1 includes a rigid, semi-rigid or flexible panel 102 sized to correspond to an interior surface, such as an inside wall 104, of the container 100. The panel 102 can be slid into the container 100 and optionally attached to the inside wall 104, such as by eyelets or loops (not shown) on the panel and hooks, screws, bolts, toggles or other suitable fasteners (not shown) on the inside wall. Other attachment mechanisms, such as adhesives or hook-and-pile systems (commercially available under the trade name Velcro®) are also acceptable. In this manner, the panel 102 can later be removed from the container 100. In any case, the panel 102 can be removably attached to the inside wall 104 or it can be permanently or semi-perma-nently attached thereto. Optionally, additional panels (not shown) can be attached to other interior surfaces, such as the opposite wall, ceiling, floor, end or doors, of the container 100. All these panels can be connected to a detection circuit, as described below. Alternatively, the container 100 can be manufactured with integral panels pre-installed therein. The panels may also be part of the container structure itself.

As noted, the panel 102 is preferably sized to correspond to the surface to which it is to be attached. For example, an ISO standard 20-foot container has interior walls that are 19.3 ft long and 7.8 ft high. (All dimensions are approximate.) Such a container has a 19.3 ft. long by 7.7 ft wide floor and ceiling and 7.7 ft wide by 7.8 ft. high ends. An ISO standard 40-foot container has similar dimensions, except each long interior dimension is 39.4 ft. ISO standard containers are also available in other lengths, such as 8 ft., 10 ft., 30 ft. and 45 ft. Containers are available in several standard heights, including 4.25 ft. and 10 ft. Other embodiments can, of course, be used with other size containers, including non-standard size containers. The panel 102 is preferably slightly smaller than the surface to which it is to be attached, to facilitate installation and removal of the panel.

The panel 102 includes an optical fiber 106 extending across an area of the panel. The optical fiber 106 can be positioned serpentine- or raster-like at regular intervals, as indicated at 108. A "pitch" can be selected for this positioning, such that the spacing 108 between adjacent portions of the optical fiber 106 is less than the size of a breach that could compromise the security of the container. Alternatively, the optical fiber 106 can be distributed across the panel 102 according to another pattern or randomly, examples of which are described below. In other embodiments, the panel 102 can be eliminated, and the optical fiber can be permanently or removably attached directly to the interior surface of the container 100. For example, adhesive tape can be used to attach the optical fiber to the interior surface. The optical fiber can be embedded within the adhesive tape and dispensed from a roll, or the optical fiber and adhesive tape can be separate prior to installing the optical fiber. In yet other embodiments, the container 100 is manufactured with optical fibers attached to its interior surfaces or sandwiched within these surfaces.

Optical connectors 110 and 112 are preferably optically attached to the ends of the optical fiber 106. These optical connectors 110 and 112 can be used to connect the panel 102 to other panels (as noted above and as described in more detail below) or to a circuit capable of detecting a change in an optical characteristic of the optical fiber. The optical connectors 110 and 112 can be directly connected to similar optical connectors on the other panels or the detector circuit. Alternatively, optical fiber "extension cords" can be used between the panel and the other panels or detector circuit.

Figure 2:
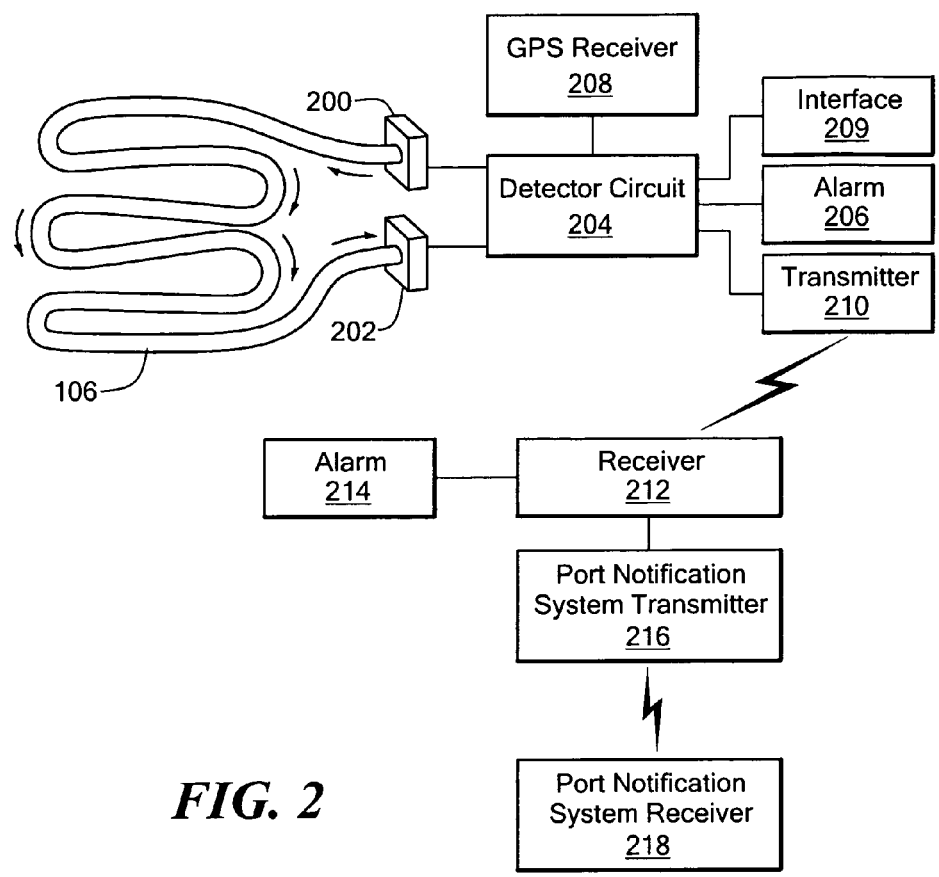
FIG. 2 is a simplified schematic diagram of major and optional components of a monitoring system, according one embodiment of the present invention.

As noted, a detector circuit is configured to detect a change in an optical characteristic of the optical fiber 106. As shown in FIG. 2, one end of the optical fiber 106 is optically connected (such as via optical connector 110) to a visible or invisible light source 200. The other end of the optical fiber 106 is connected to a light detector 202. The light source 200 and light detector 202 are connected to a detector circuit 204, which is configured to detect a change in the optical characteristic of the optical fiber 106. For example, if the light source 200 continuously illuminates the optical fiber 106 and the optical fiber is severed or otherwise damaged as a result of a breach of the container 100, the light detector 202 ceases to detect the illumination and the detector circuit 204 can trigger an alarm. Similarly, the detector circuit 204 can detect a decrease in, or complete loss of, light transmissibility of the optical fiber 106 as a result of the optical fiber being irradiated, such as by gamma rays from a radiological weapon stored in or near the optical fiber. Thus, the detector circuit 204 can trigger the alarm if the optical characteristic changes by a predetermined amount. Optical characteristic changes include, without limitation, intensity, frequency, phase, coloration of optical fiber dopants and self-annealing properties of optical fiber that has been irradiated.

The change in the optical characteristic need not be a total change. For example, in transit, as cargo shifts position within the container 100, some cargo might partially crush, compress, twist, stretch or stress the panel 102 and thereby reduce, but not to zero, the light-carrying capacity of the optical fiber 106. To accommodate such a situation without sounding a false alarm, the detector circuit 204 can trigger the alarm if the amount of detected light falls below, for example, 30% of the amount of light detected when the system was initially activated. Optionally, if the system detects a reduction in light transmission that does not exceed such a threshold, the system can send a signal indicating this reduction and warning of a likely shift in cargo or some environmental deterioration of the panel, as opposed to a breach of the container 100.

As noted, a system according to the present disclosure can be used to detect radiation from a source within or near a container. In such a system, an optical characteristic of the optical fiber is changed by radiation incident on the fiber, and this changed optical characteristic is detected. For example, if an optical fiber is exposed to nuclear radiation, the light transmissibility of the optical fiber is reduced over time due to darkening of the optical fiber. The radiation may be of various types, including alpha, beta, neutron, gamma or certain other types of electromagnetic radiation.

The light transmissibility of an optical fiber is reduced if the optical fiber is exposed to ionizing radiation, such as nuclear radiation. Radiation-induced absorption (RIA) induces ionization and creates color centers in the optical fiber, thereby reducing the optical transmissibility of the fiber. This "radiation-induced darkening" (which attenuates light signals) is cumulative over time, leading to a time-integration effect. Thus, even a low radiation dose rate over a multi-day trans-Atlantic journey would cause a detectable reduction in the transmissibility of the optical fiber. If an optical fiber that has been partially darkened by radiation is to be reused, the detector circuit 204 can calibrate itself to the fiber's then-current transmissibility when a panel containing the fiber is sealed in a subsequent container. The detector circuit 204 measures the amount of light the optical fiber transmits, and the detector triggers the alarm if it detects a further attenuation of the transmitted light. Alternatively, the radiation-darkened optical fiber can be discarded.

The degree of radiation need not necessarily be measured. Instead, only the presence or absence of radiation above a threshold can be detected to indicate the presence of a radioactive or other radiation emitting material or device. Thus, a system according to the present invention can provide a binary (Yes/No) indication of the presence of radiation because the optical fiber is either conducting light or non-conducting. Optionally, the amount of darkening of the fiber or the rate of darkening can be used to estimate the strength of the radiation source or its distance from the panel(s). Such measurements from a number of containers can be used to estimate the location of a container that houses a radiation source, such as by geometrical triangulation of different light transmissibility losses from several containers during the same time interval of measurement among many containers. For example, if a number of systems (that are roughly aligned along a line) detect progressively higher levels of radiation, the source of the radiation is likely to lie along the line in the direction of the higher radiation level. If two or more such lines intersect, the radiation source is likely to lie at the intersection.

Panels lining a typical ISO container can include as much as 29 kilometers or more of optical fiber. Because light travels the entire length of each optical path, the attenuation of this light is proportional to the sum of the lengths of all the darkened portions of the optical fibers that make up the optical path. Thus, even a small amount of radiation-induced darkening along some or all parts of the optical fiber(s) "adds up" to a detectable change in transmissibility of the fiber. Furthermore, even if a radiation source is partially shielded, such that only portions of the panels are irradiated, the system can detect the radiation source, because it does not matter which portion(s) of the optical fiber are irradiated. In particular because of the inverse square law which mathematically describes the variability of radiation intensity, should the radioactive material be close to a side of the container, there will be a non-linear favorable increase in the detection process. For example, if only a few inches of optical fiber go completely dark because of close proximity of the radioactive material source, all light in the entire length of optical fiber is blocked from reaching the light detector circuit. The most difficult point to minimize detection time is exactly in the center of volumetric space of the container. It is unlikely that the radioactive material will be in that exact spot but even if the radioactive material is at the center, the detection process still works but requires more time.

Some optical fibers are more sensitive to radiation-induced absorption than other optical fibers. Optical fiber manufacturers and others have endeavored to develop optical fibers that are less sensitive to radiation-induced absorption, such as for use in outer space, nuclear reactors and particle accelerators. These manufacturers and others have published information comparing the sensitivities of various optical fibers to radiation-induced absorption darkening (RIA), as well as fabrication techniques for making optical fibers that are less sensitive to RIA. However, these publications all teach away from the present invention, in that systems according to the present disclosure preferably use optical fibers that are much more sensitive to RIA.

Various techniques can be used to greatly increase the sensitivity of optical fibers to radiation-induced absorption.

The amount of radiation-induced attenuation experienced by a light signal carried over an optical fiber depends on the wavelength of the light signal, the type of optical fiber (single mode, multi-mode, polarization-maintaining, etc.), manufacturer, model and other factors such as dopants used in fabrication. The wavelength of the light source 200 (FIG. 2) is preferably selected to maximize the sensitivity of the optical fiber to radiation-induced darkening. Some optical fibers have two relative maximum attenuation peaks, such as at about 472 nm and about 502 nm. Other optical fibers have more than two relative maximum attenuation peaks, such as at about 470 nm, about 502 nm, about 540 nm and about 600 nm. Most optical fibers exhibit much greater attenuation at shorter wavelengths than at longer wavelengths over the working optical spectrum, thus shorter optical wavelengths are preferred. For example, if a single-wavelength light source is used, any wavelength (up to about 1625 nm or longer) can be used, however a shorter wavelength is preferred. Examples of acceptable wavelengths include about 980 nm, about 830 nm, about 600 nm, about 540 nm, about 502 nm and about 472 nm, although other relatively short wavelengths are acceptable.

Other factors, such as manufacturer and model, can also be selected for maximum sensitivity to radiation-induced darkening. For example, optical fiber available from Corning under part number SMF-28 exhibits acceptable radiation-induced darkening characteristics. Single mode, multimode, polarization-maintaining and other types of optical fibers are acceptable.

Figure 24:
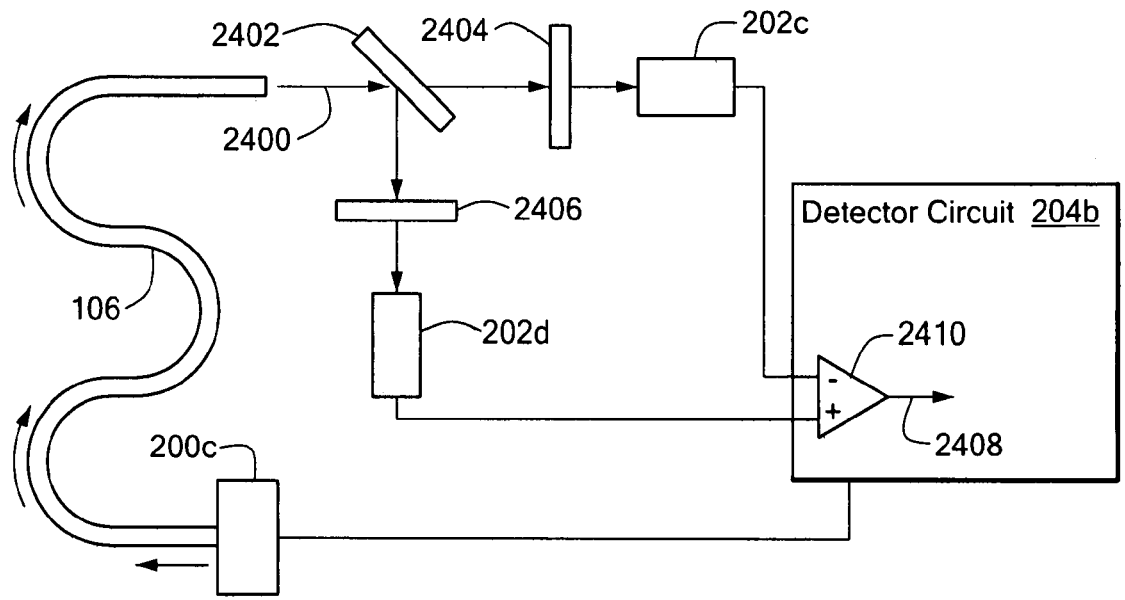
FIGS. 24 and 25 are simplified schematic diagrams of major components of monitoring systems, according other embodiments of the present invention.

Alternatively, a difference in the attenuations of short-wavelength and long-wavelength light components passing through the optical fiber can be used to trigger a detector circuit 204b, as shown in FIG. 24. If a multi-wavelength light source 200c (such as an incandescent lamp) is used, light 2400 that reaches the far end of the optical fiber 106 is split by a beam splitter 2402. One portion of the split beam passes through a first filter 2404 that passes short-wavelength light, which is then detected by a light sensor 202c. Another portion of the split beam passes through a second filter 2406 that passes long-wavelength light, which is then detected by a second light sensor 202d. For example, the first filter can pass light having a wavelength less than about 980 nm, and the second filter can pass a light having a wavelength greater than about 980 nm. A difference signal 2408 is produced by a differential amplifier 2410 from outputs of the two light sensors 202c and 202d. If the optical fiber 106 is darkened by radiation, this darkening would be more pronounced at short wavelengths than at long wavelengths, thus the output signal from the first (short wavelength) light sensor 202c would be less than the output signal from the second (long wavelength) light sensor 202d, and the difference between the signals from the light sensors would be detected by the differential amplifier 2410. Just before or after sealing a container, the difference between the signals is noted and stored, such as in a memory (not shown) in the detector circuit 204b. Later, if the difference between the signals increases, for example if the difference exceeds a predetermined threshold, the alarm is trigger.

Of course, the differential amplifier 2410 can be replaced by any circuit or software that compares the signals from the light sensors 202c and 202d or calculates a difference between the signals. For example, two digital-to-analog converters (DACs) can be respectively connected to the light sensors 202c and 202d, and outputs from the DACs can be digitally compared or one of the outputs can be digitally subtracted from the other output, and the difference can be compared to a threshold value.

Figure 25:
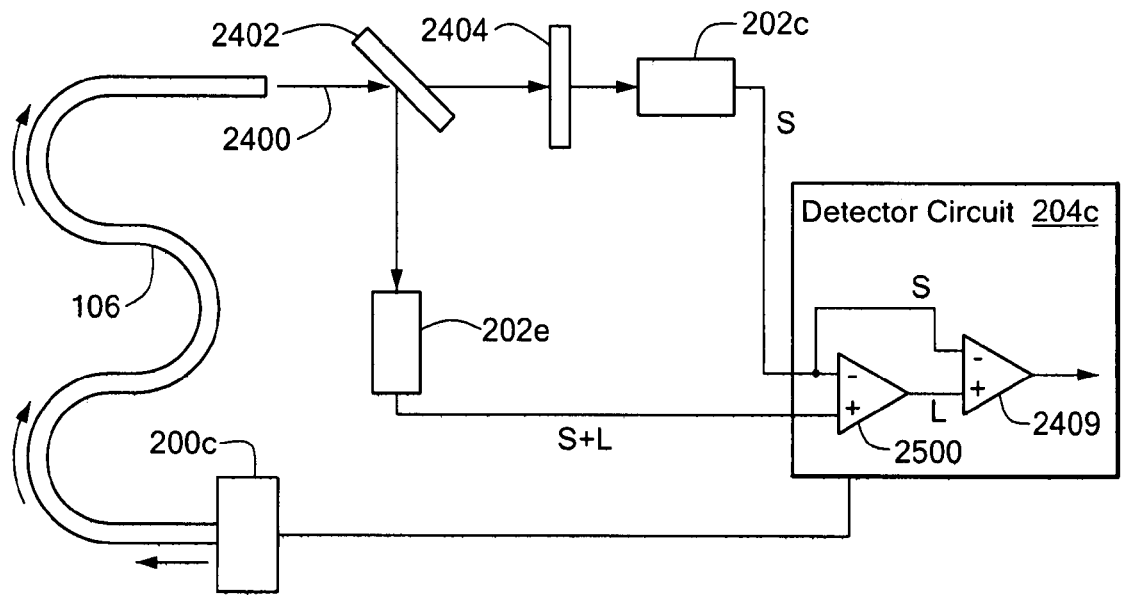

Alternatively, as shown in FIG. 25, one of the filters can be omitted. In this case, the filter 2404 passes short-wavelength light, which is detected by the light sensor 202c to produce a short-wavelength signal S, as discussed above. The other light sensor 202e is unfiltered, thus it detects both short-wavelength light and long-wavelength light to produce a short- and long-wavelength signal (S+L). A first differential amplifier 2500 of detector circuit 204c produces a difference signal (S+L)−S=L that represents the amount of long-wavelength light emerging from the optical fiber 106. A second differential amplifier 2409 operates as discussed above to produce a signal that represents the difference between the amount of short-wavelength and long-wavelength light emerging from the optical fiber 106.

Thermal annealing can release charges trapped within an optical fiber, thus at least partially reversing the effect of radiation-induced absorption. However, this thermal annealing can not occur at cold temperatures, such as those likely to be encountered during an ocean-going voyage in cool climates. To minimize the temperature of a container, and thus minimize thermal annealing of the optical fiber, the container can be loaded low in the hold of a ship or below other containers to reduce or eliminate sunlight shining on the container. The average temperature of the container is preferably kept less than or equal to about 25° C.

Some published information suggests using radiation-induced attenuation to measure radiation in optical fiber-based dosimeters, however such systems rely on thermal annealing to enable the optical fiber to quickly recover after being irradiated and be used for subsequent measurements. Thus, these publications teach selecting or constructing optical fibers that exhibit good recovery characteristics. These publications teach away from the present invention, in that systems according to the present disclosure preferably use optical fibers that have poor recovery characteristics and/or are operated so as to minimize or prevent recovery.

Radiation sensitivity of optical fiber is highly dependent on dopants used in the manufacture of the fiber. Typical dopants include erbium, ytterbium, aluminum, lead, phosphorus and germanium. dopants, such as phosphorus, that increase the index of refraction of the core of the fiber are particularly influential in increasing the radiation sensitivity of optical fiber. Radiation sensitivity increases with erbium content. In addition, greater aluminum oxide content in the core of an erbium-doped optical fiber increases the sensitivity of the fiber to radiation-induced effects. For example, an optical fiber doped with about 0.18 mol % Yb, about 4.2 mol % $Al_2O_3$ and about 0.9 mol % $P_2O_5$ exhibits an order of magnitude more attenuation than an optical fiber doped with almost the same amounts of Yb and $P_2O_5$ but only about 1.0 mol % $Al_2O_3$.

Lanthanum can also be used as a dopant. For example, an optical fiber doped with about 2.0 mol % La and about 6.0 mol % $Al_2O_3$ is extremely sensitive to radiation-induced effects, compared to Yb-doped and Er-doped optical fibers. The optical fiber preferably includes one or more of the dopants listed above to increase or maximize its sensitivity to radiation.

Ytterbium-doped optical fiber and germanium-doped optical fiber can become "saturated" with radiation-induced absorption. When saturated, the annealing affects and the radiation-induced trapped charges balance, such that the radiation-induced attenuation reaches a constant value, even in the face of increasing total radiation dosage (at a constant dose rate). The predetermined amount, by which the optical characteristic must change before the detector circuit 204 triggers the alarm, should take into account this saturation. Thus, the detector circuit 204 triggers the alarm preferably before the optical fiber becomes saturated.

Fluorine and boron are sometimes used to lower the index of refraction of optical fiber cladding. When it is used to dope the core of an optical fiber, fluorine increases radiation resistance, so optical fibers without fluorine or with minimal fluorine in the core are preferred.

Naturally-occurring, background ionizing radiation, which measures about 300 millirems per year in the United States, can have a long-term effect on the transmissibility of optical fiber. The detector circuit 204 can account for a slow degradation in the optical fiber's transmissibility as a result of this background radiation, so the detector circuit does not generate false alarms.

Figure 3:
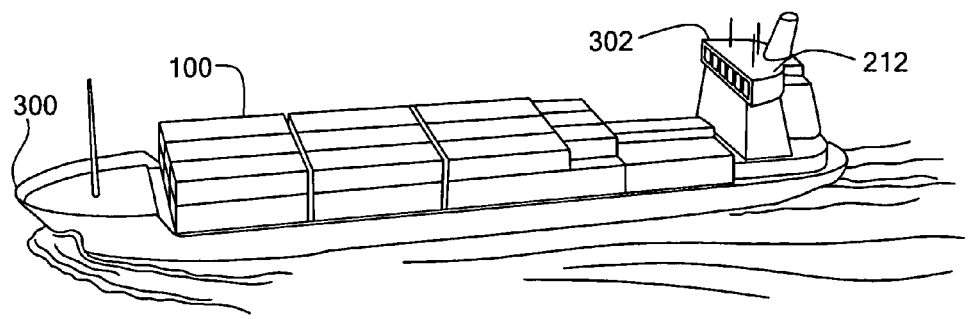
FIG. 3 is a perspective view of one context in which embodiments of the present invention can be advantageously practiced.

Gamma radiation easily penetrates the metallic walls of shipping containers. Thus, a system disposed within one container can detect radiation from a source within the container, as well as from a source in a nearby container, even if the nearby container is not equipped with its own radiation detection system. In transit, containers are typically stacked side-by-side and on top of one another, as shown in FIG. 3. Thus, gamma radiation from one container is likely to be detected by systems in adjacent containers. The number and positions of the adjacent containers where radiation is detected depend on several factors, including the strength of the radiation source, the number and thicknesses of intervening metallic walls of other containers and the time-integration period over which the radiation impinges on the optical fibers. Even if the container that houses the radiation source is not equipped with a radiation detection system, the locations and pattern of containers whose systems detect radiation (and optionally the amount of radiation detected by the respective systems) can be used to identify the location of the radiation-emitting container by geometric triangulation of multiple container detections within the same time interval of measurement.

Radiation of various types, such as: Gamma, X-Ray, Beta, Alpha and Neutron particles can reduce, alter, or interrupt the transmission of many different types of light that may be used to produce a light signal transmission in an optical fiber path.

In order to enhance the detection of incident radiation within a cargo container on the optical fiber path lining the inside of the container, the light source may be turned on and off on a cycled basis, such that the light source emits a coded sequence of light pulses. By way of example: assume a terrorist has secreted a radiological weapon in a container, at the time it is legitimately loaded. (If it were secreted after legitimate loading, the act of physical intrusion would immediately set off the alarm.) The radiological weapon will be in transit say for two weeks before it is timed to detonate at its port of destination. The sequence of light pulses could, by way of example, consist of a series of 10 pulses turned on for a brief sampling period at the beginning of each of the 336 hours (or less) comprising the transit time in hours of the cargo shipment. Each series of 10 pulses could encode a 10 bit binary number having an accuracy of 1 part in 1012 i.e. 1 binary bit in 10 bits. Through the use of a suitable microprocessor unit and logic circuits readily known to those skilled in the art, the detection of each train of received light pulses at the photodetector circuit could be analyzed and compared to prior trains of pulses emitted on a prior periodic basis in order to determine if the binary number represented by the pulse trains remains constant. Each binary number measurement can be compared to the previous measurement, or some running average of previous measurements to determine if the measurement has changed. The detection of continuous or otherwise sufficient change in the sequence of measurements can be employed to trigger an alarm condition. If there is a succession of measured light pulse trains, the designated periodic sampling basis of say 1 hour, (by way of example) will show a steady degradation in number value between a binary value of 1012 maximum to a binary minimum value of 0 (i.e. 10 bit spread in value), approximately one thousand to one; which will indicate on a quantitative basis that there is a continuous process of degradation of light transmission between the light source over the single continuous optical fiber pathway to the photodetector circuit. This will correlate with real-time impairment of the light transmissibility of the particular type of the optical fiber used in the liner panels because of the well-known effects that radiation will irreversibly darken certain types of optical fiber. Various coding schemes can be employed to provide alarm detection upon a predetermined change in code pattern or other characteristic, which coding schemes are themselves known in the art of communications.

Well-known mathematical statistical techniques can be used to determine in real-time certain trend lines which show on a simple yes/no basis, detection of the presence of radiation through its effect on the light signals being transmitted in the optical fiber. This yes/no basis of detection describes the system as an effective binary switch i.e. the optical fiber is conducting light or it is not conducting light. The determination of linear decreasing slope line, or complex radius of curvature of non-linear decreasing slope line, may be constructed from the array of binary data ascertained by the periodic sampling and measurement of light pulses transmitted over the optical fiber path in the presence of a radiation field within the cargo container or through the wall to an adjacent container. The decreasing slope line correlates directly with the rate of optical fiber darkening induced by radiation.

In another embodiment, binary bit patterns of light pulses are transmitted through the optical fiber and an error rate is detected at a far end of the optical fiber. The binary bit patterns can modulate the light pulses in various ways, such as ON/OFF pulses, changes in frequency (i.e., color shifts), changes in polarity, changes in phase or other changes or combinations of changes in one or more characteristics in the light transmitted through the optical fiber. The errors are caused by a change in an optical characteristic of the optical fiber, such as a decrease in the light intensity of the optical transmissibility of the fiber. As the optical transmissibility of the fiber decreases (due to continued exposure to radiation), the error rate increases. The rate of increase of the error rate, can be specified as a "profile" of the error rate over time which is proportional to an integration of the amount of radiation than has darkened the optical fiber. This profile can be accurately correlated to known decay profiles (due to half lives) of various radioactive nuclear isotopes to identify the isotope(s) that produced the radiation that darkened the fiber and the amount(s) of the(those) isotope(s). Thus, the isotope can be identified by essentially measuring 2 key parameters. One parameter is the half-lifetime constant of decay, given by the single equation which describes all radioactive decay processes, $N=N_o \exp(-\gamma t)$, where $\gamma$ is the decay constant unique to a particular radioactive isotope. Additionally the mass of radioactive isotope present during the measurement interval will correlate to the rate of darkening of the optical fiber in accordance with the inverse square law of distance between the radiation source and the light detector. The solid angle of impinging radiation source on the optical fiber will be known because the single continuous optical fiber system totally encapsulates the source.

Radiation-damaged optical fiber causes a change in polarization of light transmitted by the fiber because the delicate atomic and molecular crystalline structures of the optical fiber are damaged by absorption of radiation. Illuminating one end of the fiber with polarized light, and detecting the amount of light having the same polarization that reaches the far end of the fiber increases the sensitivity of the system to radiation, because the radiation-damaged fiber acts like a polarization filter that is rotated, so the filter is not lined up with the polarization of the illuminating light (or the sensor at the far end). Thus, less light (of the expected polarization) is detected at the far end of the radiation-damaged fiber. Furthermore, as the fiber is increasingly damaged by ongoing radiation exposure, the fiber causes increasing change in the polarization of the transmitted light, and less light is detected at the far end of the radiation damaged fiber.

Alternatively, the polarization of the light at the far end can be measured. The change in the polarization angle (from that of undamaged fiber) is proportional to the amount of radiation-induced damage the fiber has undergone.

Light transmitted by an optical fiber is transmitted as two orthogonally-polarized components. One component is transmitted faster than the other component. The relative speeds of these components is different in non-radiation-damaged optical fiber than it is in radiation-damaged fiber. This difference can be used to measure the amount of radiation-induced damage that has occurred to the fiber, which is proportional to the amount of radiation the fiber has been subjected to.

Any combination of the herein-described techniques to detect radiation-induced damage to optical fiber can be used. For example, a change in polarization angle can be measured, along with a change in the intensity of all light (regardless of polarization) received at the far end, to ascertain the amount of radiation damage the fiber has undergone.

It is understood that the optical fiber used in this invention is irreversible i.e. it cannot self anneal like "hardened" optical fibers which are designed to recover their light transmission properties, otherwise there will be an undesirable recovery in light transmission, which will alter the radiation induced degradation detection process in an unpredictable manner.

Since a radioactive nuclide will spontaneously transform into a daughter nuclide, which may or may not be radioactive, according to the well known formula $N=N_o \exp(-\gamma t)$, it is desirable to be able to analyze the degradation of the light transmission in the optical fiber using an analysis technique to easily detect the decay rate of an exponential function. This can be done using a logarithmic scale amplifier to convert a sequence of binary pulse numbers for comparison to prior samples in such a way as to make such logarithmic number sequence linear with respect of one sequence to another, or with respect to a time base. It is also possible to set the sampling periods of the measured light pulses on an exponential time basis rather than on a linear time basis, which will have the effect of producing linear samples of pulses and resultant light transmission detection values which correlate with the radiation induced darkening of the optical fiber.

For purposes of detection, the objective is to show a continuous degradation of light pulse signals from the photoemission light source to the photodetector circuit over periods of time that are short with respect to the transit time for the cargo container, which may be holding a secreted radioactive material. If the half-life of the radioactive material, which is described by the well-known formula $N=\frac{1}{2}N_o$, is comparatively close to the time interval of the container transit time, during which sampling is taking place, the data detection numbers of decreasing light transmissibility of the optical fiber will resemble an exponential function. (Note-short half-life radioactive materials normally used in medical and industrial applications are the most likely available sources of material for illicit construction of radiological weapons). If the half life of the secreted radioactive material is long compared to the transit time of the container, the data detection numbers of decreasing light transmissibility will be much more linear i.e. representing a small segment of an exponential function with a long half life, such as found in weapons grade nuclear bomb material, such as uranium or plutonium.

The rate of attenuation of light in the optical fiber pathway, i.e. darkening of the optical fiber, will be in some linear or non-linear proportion to the amount of radiation absorbed by the optical fiber. Because of the specific characteristics of the optical fiber employed, the optical fiber will not have self-annealing properties nor in any way have chemical or physical mechanisms in the optical fiber which allow it to recover from the effects of radiation absorption beyond a certain level of normal environmental radiation, which global average is 300 millirems per annum. The specific amount of radiation activity; determined by the amount of radioactive material, its distance to the surrounding optical fiber, according to the inverse square law the type of radioactive material (which isotope etc.) and the half life of the radioactive material, will correlate mathematically with the darkening of the optical fiber by the absorption of this radiation into the chemical and physical atomic and molecular crystalline structures of the optical fiber. The irreversible darkening of the optical fiber results in loss of light transmission for the light source through the single continuous optical pathway to the optical photodetector. This loss of light transmission can be measured by suitable electronic devices and accurately described as a power loss in decibels, which is a well-understood engineering term used to describe loss of light in optical fiber transmission. It is well known that many radioactive processes are very complex, and certain materials which have low levels of energy associated with their emission of particles, can in turn transmute into daughter radioactive nuclides with high levels of energy associated with their emission of particles. This can either have no effect on the detection process or speed up the detection process, since all radioactive emissions will be cumulative in darkening the optical fiber. Alternatively the detection of ramp-up rates of darkening of the optical fiber can be used to identify parent/daughter sequences to identify specific radioactive materials. A detectable loss of light transmission is used to trigger an alarm signal.

Light is degraded during transmission due to attenuation, polarization, and dispersion. No matter how cleverly optical fiber is drawn during manufacturing there is a certain level of polarization mode dispersion (PMD) inherent in the optical fiber. When light is injected into an optical fiber, the light usually splits into two different polarization planes, and each polarization component travels down the fiber. The two perpendicular polarizations will travel at different speeds and arrive at different times i.e. a fast axis and a slow axis. When radiation induces damage to the atomic or molecular crystalline structure of the optical fiber utilized in the present invention, which is irreversible and has no self annealing mechanism, the transmission of polarized light will be much more difficult to detect because of increased dispersion within the optical fiber. This effect makes the radiation-induced damage to the optical fiber easier to be detected if the transmitted light signal is polarized. This phenomenon results because in the fabrication of single mode optical fibers, it is impossible to fabricate a perfectly round core and free from all stresses. If this was possible, both polarization modes would propagate at exactly the same speed, resulting in zero PMD. Radiation exacerbates the unavoidable imperfections of the glass/silicon fabrication process.

One embodiment of the disclosed system records the light transmissibility of the optical fiber (or the attenuation through the optical fiber) over time. The rate of change or the "profile" of that change over time is characteristic of the decay of the isotope or combination of isotopes or other sources that produce the radiation that causes the darkening of the optical fiber. The system stores, such as in a microchip memory, a library of expected profiles which were experimentally determined for various isotopes, combinations of isotopes and/or other radiation sources. After recording changes in the transmissibility of the optical fiber, the system compares the recorded profile to the library of profiles for a matching profile. Based on the matching profile, the system can determine the identity of the radiation source. Optionally, based on the rate of change of the profile (rate of change in transmissibility), the system can estimate the amount of radioactive material present.

Using polarized light as a source, optimally in combination with measurements on a fast axis and slow axis, can be used to amplify the sensitivity of the detection process due to radiation darkening of the optical fiber. Polarized light will have a more difficult time being transmitted in the optical fiber and detected as opposed to non-polarized light. Just as light transmission is impaired by rotating two adjacent polarizing filters through which light is being transmitted, radiation induced changes in the optical fibers crystalline structure causes increased light dispersion, amplifying the difference in transmission times between the fast axis and slow axis. The effect is a diminution of light transmissibility just as rotating two polarized filters with decrease light transmission.

This is not dissimilar to the use of short wavelengths to increase detection sensitivity of radiation damage in optical fiber as opposed to using longer wavelengths of transmitted light.

Major benefits of this system over current methods of scanning cargo containers from the outside are as follows:

1) Passive scanning from the inside perimeter on six sides inwards always preserves exact geometry of the scanning process which is necessary for reliable scanning results. Moving containers past fixed radiation detection pylons, or manually moving a hand held detector around a container, means there will be variable geometry of measurements and the inability to perform measurements to exacting standards in order to have a front line scanning methodology for all containers which is accurate for each container. Additionally because of the inverse square law, should a radiation source be close to a side of the container, there will be a much more rapid decrease of the light signal due to more intense darkening of the closest segment of optical fiber. Though the single continuous optical fiber pathway may in fact be 29 km long, if a single small segment of the optical fiber goes dark, no light can pass through the optical fiber, and the absence of detected light will cause the alarm signal. This "near proximity" of a radioactive source to a wall of a container may be likened to a single car breakdown on a one lane highway. The optimal strategy to minimize detection of the radiation source would be to place it exactly in the center of the container which is an unlikely occurrence. Since the maximum distance to the center of the container from a fiber optic panelled wall is four feet, the detection process may take a little more time, but cannot be avoided.

2) Current practices use expensive high performance instruments, which are not well suited, nor economical for first line of defense monitoring. The instruments give "information overload", and have to be constantly calibrated and field maintained, and are too complex for untrained personnel to use. What is a far more effective and resource efficient methodology is to break the monitoring into two parts; first detect a problem container, and secondly upon such detection, inspect the subject container. Both steps are not needed for every container since only very few containers will be "hot" and require more detailed analysis or inspection. This method can be likened to putting an "optical fuse" in each container. If the "fuse blows" an inspection is mandated.

3) The length and mass of the fiber i.e. one to 29 km or more of optical fiber in the container from small to large size presents a massive detection array surrounding the radiation source, with exact geometry which significantly sensitizes and simplifies the detection process. Additionally, since optical fiber is quite inexpensive, the density of the optical fiber in the liner panels can be significantly increased by the use of multiple fibers overlaying one another in one or more panels, each slightly shifted to give almost continuous physical coverage of optical fiber as it receives the impact of the radiation. For example, the fiber can be woven into a fabric which is embedded or otherwise disposed in a panel, and multiple fabrics can be overlayed in offset manner to provide an intended path between adjacent fibers. Or panels each having a fiber path thereon can be offset. This has the effect of presenting an increase in physical size of the detector intercepting the solid angle of radiation from the source of radioactivity. This will significantly enhance the radiation detection process. A similar effect can be had by tightening the bend radius of the optical fiber in the sensor panel by using optical fiber that is made to withstand a smaller bend radius without loss of light. Such augmentation also will result in a much smaller resolution of physical intrusion detection down to as small as ¼ square inch on any side of the container.

4) Because this system continuously "looks" at the radiation source for up to the period of container transit time, such as a two week period, the ratio of this sample time interval to current "wave-by" wanding or pylon measurement times is up to an amplification of 50,000 to 1. This dramatically increases the capability of detecting very low levels of radiation. A low-level radiation source placed in the container, in effect becomes a detector box to "cook" the optical fiber over a long exposure time interval. Because radiation activity is cumulative, this dramatic increase of sampling time interval greatly sensitizes the detection process, especially for low levels of radioactive material, as it "cooks" in the container.

5) Active scanning, as opposed to passive scanning, such as by use of X-rays, gamma rays or neutron scanning, can be catastrophic if there is a nuclear or radiologic weapon in the container. It is possible that terrorists would booby trap such a weapon, rather than let it be captured. There are many ways to detect active scans using simple crystal circuits as a triggering device and such detectors could trigger a weapon secreted in a container.

Known active scanning technologies for detection of physical intrusion through the sides of a container, consist of scanning with radiowaves in the millimeter range or by the use of sound waves. These techniques all have a spatial resolution of intrusion through a continuous surface fixed by the energy of the scanner and specific mechanism of scanning. Thus, breaking up a continuous surface into a finite number of "pixels" is highly variable in fixing the size of a physical intrusion. In contrast, a major benefit of the novel system is that by the use of liner panels with embedded optical fibers, the "pixel" size of resolution is accurately and reliably imposed as a static specification on the continuous surface of the inside wall(s) of the container. In addition, the invention does not employ active scanning and does not have the disadvantages of active scanning noted above.

Nuclear materials typically generate heat as they decay; in particular if they are Alpha or Beta emitters. If a nuclear material were to be stored or shipped inside a suitably thermally insulated container, the heat generated by the nuclear material would over time increase the temperature inside the container. This in particular is true for plutonium with a half-life of 24,000 years, which is about ½% of the half-life of uranium-a much more difficult detection requiring long sample times of cummulation. For example, a high thermal barrier, i.e. a material with a high R rating, such as reflective foil or foam (which can be part of the liner panels described herein) can be used to thermally insulate a container. In one embodiment, one or more heat sensors detect the temperature within the container or the temperature gradient between the inside of the container and the outside of the container (or across the thermal insulation). If the sensor (or the circuit) detects a temperature or temperature gradient that exceeds an expected value, the system determines that nuclear material (or some other unexpected heat source, such as a stowaway, a reactive exothermic chemical, or a fire) is present within the container.

Alternatively, the system can compare the internal temperatures of several adjacent or nearby containers to determine if one of the containers has a higher internal temperature than its neighbors. A relatively "hot" container can be identified as containing nuclear material or another unexpected heat source. Temperature measuring devices with very high resolution are readily available on an inexpensive basis. The output of a temperature measurement above a predetermined level would constitute an alarm signal, as previously described, such as a yes/no alarm signal that could be used to turn off the light source in the optical pathway, thereby causing the photodetector to detect an absence of light and transmit an alarm signal to a monitoring station.

The heat output of nuclear material follows the same characteristic curve as the radiation (i.e. decay) curve. Thus, the rate of change or the profile of the temperature (or temperature gradient) can be used to identify the isotope or amount of nuclear material present, as discussed above with respect to the profile of optical transmissibility. The rate of change or profile can also be used to distinguish between a nuclear heat source and another heat source, such as a fire. For example, an internal container temperature caused by a fire rises much more rapidly than an internal temperature rise caused by a nuclear material.

As noted, the transmissibility of optical fiber is reduced as a result of exposing the fiber to nuclear or other ionizing radiation. This decrease is gradual over time. The darkening of optical fiber can, however, be reversed. For example, high temperatures can anneal optical fiber that has been radiation-darkened. High-temperature annealing takes more time than radiation-induced darkening. In addition, high temperature annealing also makes optical fiber resistant to radiation-induced darkening. Thus, high-temperature annealing also "hardens" the fiber to radiation. Optical fiber exposed to significant heat produced by nuclear material within a container experiences such high-temperature annealing and/or hardening. Thus, the optical fiber is darkened by the radiation, then annealed by heat and hardened against re-darkening.

Figure 32:
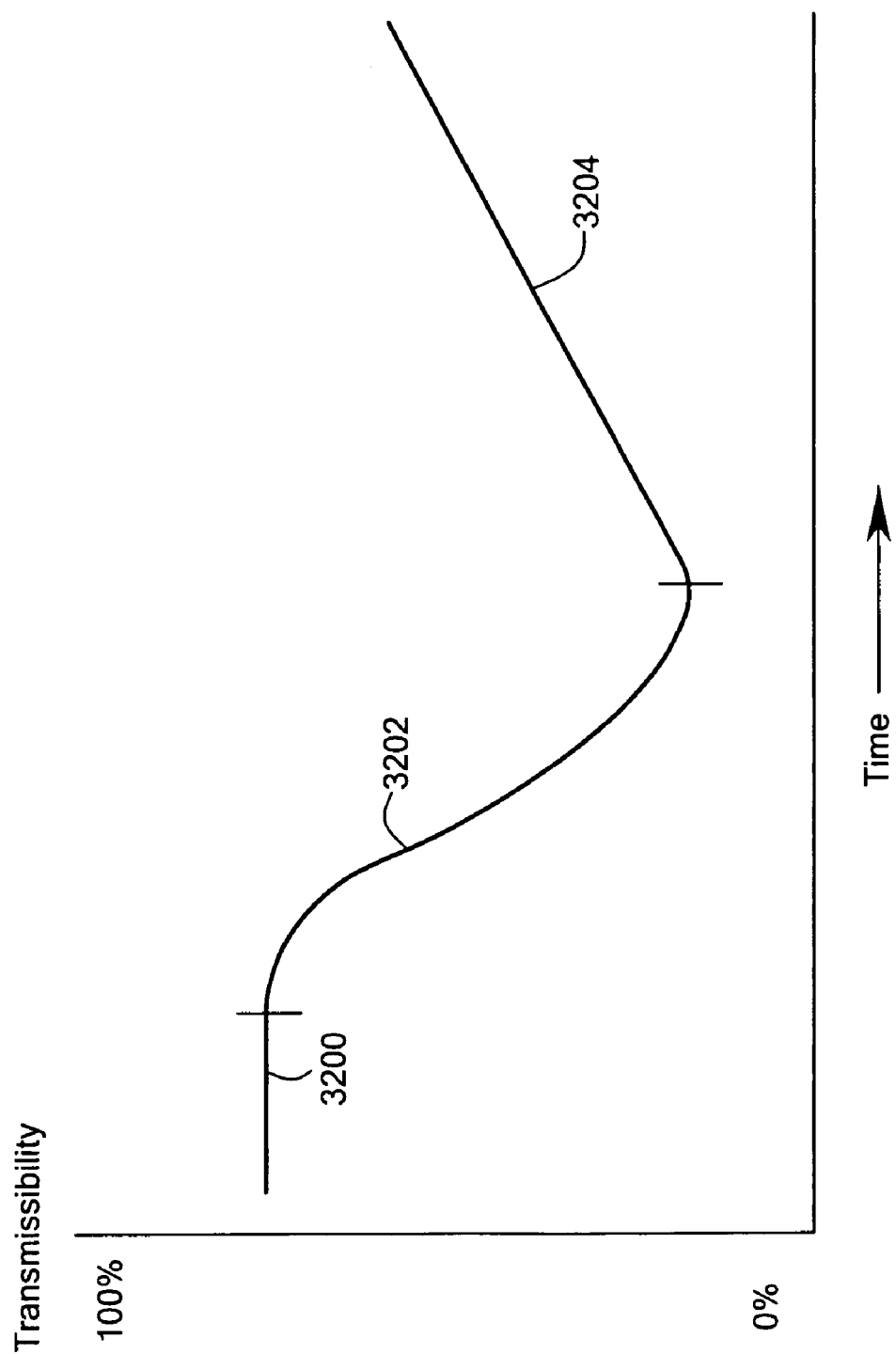
FIG. 32 is a plot of light transmission over time of an optical fiber exposed to nuclear radiation.

These characteristics of optical fiber can be exploited to detect radiation within a container or from a nearby container. For example, the transmissibility of an optical fiber exposed to nuclear radiation follows a curve, as shown in FIG. 32. Initially, such as at 3200, before being exposed to the radiation, the optical fiber has high transmissibility. As the fiber is exposed to the radiation, the transmissibility of the fiber decreases, as shown at 3202. Later, as the optical fiber is high-temperature annealed, the transmissibility increases, as shown at 3204. However, the increase in transmissibility 3204 occurs more slowly than the decrease in transmissibility 3202.

Some embodiments store information representative of the profiles of transmissibility, as shown in FIG. 32. These embodiments compare measured changes in transmissibility to the stored profiles to detect nuclear radiation and, optionally, to identify the isotope and/or amount of nuclear material present.

Embodiments of the present invention can detect a breach of the interior surface of a shipping container or box or radiation from a source within or near the container or box and can then trigger an alarm or notify a central monitoring location, such as a ship's control room or a port notification system. At least one liner sheet lines at least a portion of at least one interior surface of the shipping container or box, such that a breach of the portion of the interior surface also damages the liner sheet or radiation from a source, such as a nuclear or radiological weapon, impinges on the liner sheet. Such a liner sheet can also be attached to other perimeter surfaces, such as fences or building walls, to detect a breach of a surface or radiation near a surface. The liner sheet defines an optical path extending across at least a portion of the sheet. The optical path is monitored for a change, such as a loss or reduction of continuity, in an optical characteristic of the optical path or a change in a characteristic of the light signal, such as a frequency or phase shift. If the container, box interior or other monitored surface is breached or the optical path is irradiated, one or more portions of the optical path are affected and the optical path is broken or altered. For example, a breach of the container or box can break the optical path. Alternatively, radiation can reduce or alter the light transmissibility of the optical path. The detected change in the optical path can be used to trigger an alarm, such as an annunciator or cause a notification signal to be sent to a monitoring station via any of a wide variety of existing networks, such as the Internet and/or a wireless telecommunications network. In addition, a detailed accompanying message can provide information about the nature of the breach, time, location, cargo manifest, etc.

Returning to FIG. 2, the detector circuit 204 and other components of the tamper detection system that reside in the container 100 can be powered by a battery, fuel cell, thermocouple, generator or other suitable power supply (not shown). Preferably, the power supply is disposed within the protected portion of the container, so the power supply is protected by the tamper detection system. A reduced light signal can forewarn of a pending failure of the power supply or attempt at defeating the tamper detection system. If power is lost, the absence of the light signal will cause the alarm. The absence or loss for any reason of the light signal will cause an alarm condition. For example, if the antenna on the outside of the container is damaged of sabotaged, the failure of detected signal can trigger the alarm. As another example, an attempt to cover the entire container with a metallic curtain such as a Faraday cage will block transmission and cause an alarm condition after a test or heartbeat signal is sent for system monitoring purposes. Thus, any loss in communication with the container can be an indication of an alarm condition.

Alternatively, rather than continuously illuminating the optical fiber 106, the detector circuit 204 can control the light source 200 to provide modulated or intermittent, for example pulsed, illumination to the optical fiber 106. In this case, if the light detector 202 ceases to detect illumination having a corresponding modulation or intermittent character, or if the light detector detects light having a different modulation or a different intermittent character, the detector circuit 204 can trigger the alarm. Such non-continuous illumination can be used to thwart a perpetrator who attempts to defeat the tamper detection system by illuminating the optical fiber with a counterfeit light source.

The detector circuit 204 can be connected to an alarm 206 located within the container 100, on the exterior of the container, or elsewhere. The alarm 206 can be, for example, a light, horn, annunciator, display panel, computer or other indicator or a signal sent over a network, such as the Internet. Optionally, the detector circuit 204 can be connected to a global positioning system (GPS) 208 or other location determining system. If so connected, the detector circuit 204 can ascertain and store geographic location, and optionally time, information when it detects a breach or radiation or periodically. The detector circuit 204 can include a memory (not shown) for storing this information. The detector circuit 204 can also include an interface 209, such as a keypad, ID badge reader, bar code scanner or a wired or wireless link to a shipping company's operations computer, by which information concerning the cargo of the container 100 can be entered. This information can include, for example, a log of the contents of the container 100 and the locations of the container, when these contents were loaded or unloaded. This information can also include identities of persons who had access to the interior of the container 100. Such information can be stored in the memory and provided to other systems, as described below.

Optionally or in addition, the detector circuit 204 can be connected to a transmitter 210, which sends a signal to a receiver 212 if the detector circuit detects a change in the optical characteristic of the optical fiber 106. An antenna, such as a flat coil antenna 114 (FIG. 1) mounted on the exterior of the container 100, can be used to radiate the signal sent by the transmitter 210. The receiver 212 can be located in a central location or elsewhere. In one embodiment illustrated in FIG. 3, the container 100 is on board a ship 300, and the receiver 212 is located in a control room 302 of the ship. Returning to FIG. 2, the receiver 212 can be connected to an alarm 214 (as described above) located in a central location, such as the ship's control room 302, or elsewhere.

Some ships are equipped with automatic wireless port notification systems, such as the Automatic Identification System (AIS), that notify a port when such a ship approaches the port. Such a system typically includes an on-board port notification system transmitter 216 and a receiver 218 that is typically located in a port. The present invention can utilize such a port notification system, or a modification thereof, to alert port officials of a breached container or a container in or near which radiation has been detected and optionally of pertinent information concerning the container, such as its contents, prior locations, times of loading/unloading, etc. The receiver 212 can store information it has received from the transmitter 210 about any containers that have been breached in transit or in which radiation has been detected. This information can include, for example, an identity of the container, the time and location when and where the breach occurred or radiation was detected, etc. The receiver 212 can be connected to the port notification transmitter 216, by which it can forward this information to the port at an appropriate time or to a terrorism monitoring system in real time. Other communication systems, such as satellite communication systems or the Internet, can be used to forward this information, in either real time or batch mode, to other central locations, such as a shipping company's operations center.

Alternatively or in addition, the transmitter 210 can communicate directly with a distant central location, such as the port or the shipping company's operations center. In such cases, a long-range communication system, such as a satellite-based communications system, can be used. In another example, where the container is transported over land or within range of cellular communication towers, cellular communication systems can be used. Under control of the detector circuit 204, the transmitter 210 can send information, such as the identity of the container and the time and location of a breach or radiation detection, to the central location. Optionally, the transmitter 210 can send messages even if no breach or radiation has been detected. For example, the detector circuit 204 can test and monitor the operational status of the tamper detection system. These "heart beat" messages can indicate, for example, the location and status of the tamper detection system, such as condition of its battery or status of an alternate power supply, such as remaining life of a fuel cell, or location of the container. Such periodic messages, if properly received, verify that components external to the container, such as the antenna 114, have not been disabled.

As noted above, and as shown in FIG. 4, several liner sheets, examples of which are shown at 400 and 402, can be connected together to monitor several interior surfaces of a container or to monitor a large area of a single surface. These liner sheets 400-402 preferably include optical connectors 404, 406, 408, and 410. Optical paths, for example those shown at 412 and 414, defined by the liner sheets 400-402 can be connected together and to the detector circuit 204 and its associated components (shown collectively in a housing 416) via the optical connectors 404-410. Optical fiber "extension cords" 418 and 420 can be used, as needed. If the optical paths 412-414 were connected together in series, a breach of any liner sheet 400 or 402 would trigger an alarm.

The intensity of the input light and the sensitivity of the detector can be such that no amplifiers or repeaters are necessary along the optical path for a simple yes/no determination of breach of the container. Alternatively, each panel or a group of panels can have a respective optical path and associated light source and detector, such that a breach of the optical path of the container panels can be identified with a particular panel or side of the container.

Figure 5:
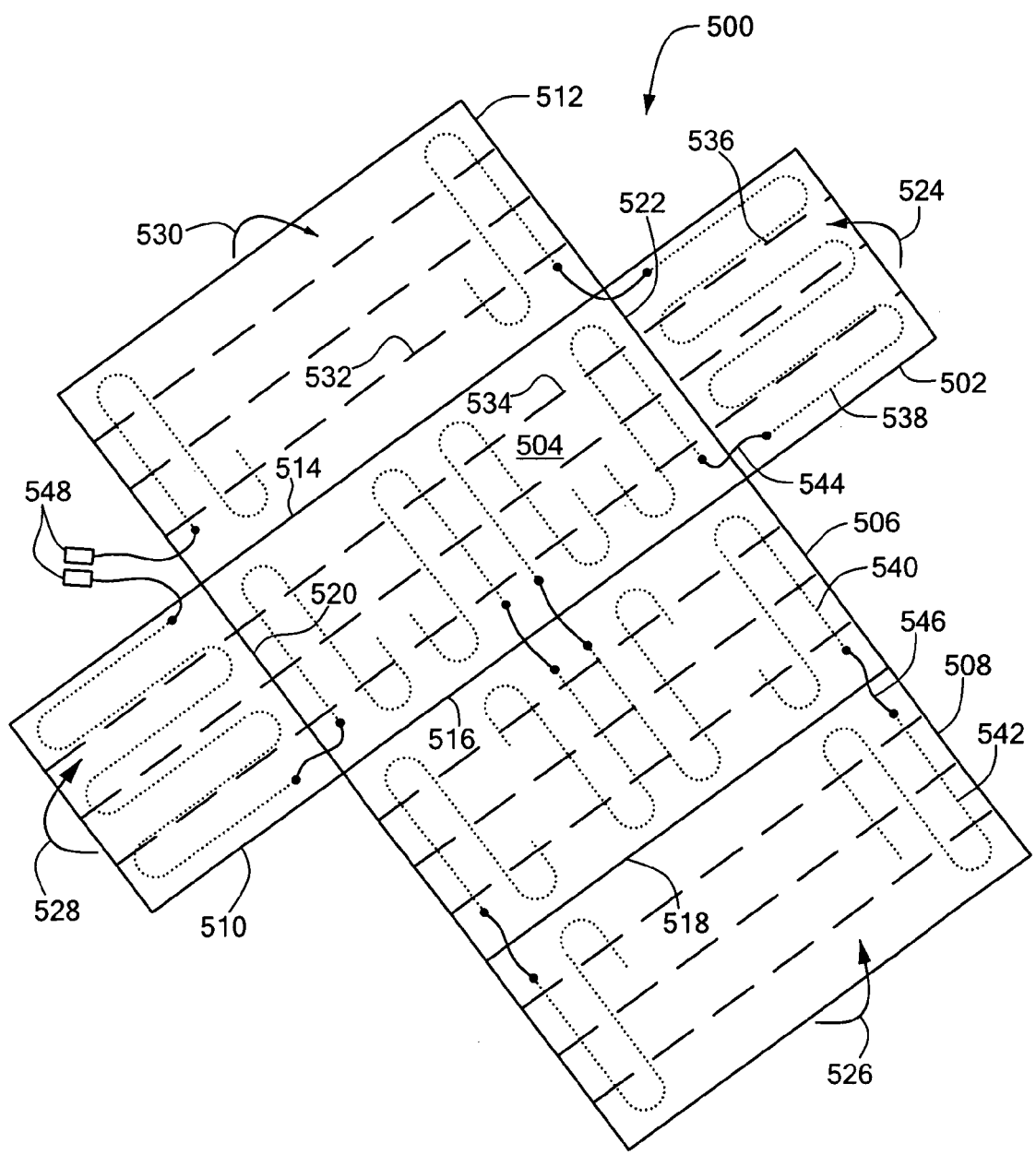
FIG. 5 is a perspective view of a six-panel, hinged liner sheet, according to another embodiment of the present invention.

In another embodiment illustrated in FIG. 5, a single liner sheet 500 can include several hinged panels 502, 504, 506, 508, 510, and 512. The panels 502-512 can be folded along hinges 514, 516, 518, 520, and 522 (as indicated by arrows 524, 526, 528, and 530) to form a three-dimensional liner for a container. Once folded, the liner sheet 500 can, but need not, be self-supporting and thus need not necessarily be attached to the interior surfaces of the container. For example, hinged panel 512 (which corresponds to a side of the container) can attach to hinged panel 508 (which corresponds to a ceiling of the container) by fasteners (not shown) mounted proximate the respective edges of these panels.

Similarly, hinged panels 502 and 510 (which correspond to ends of the container) can attach to hinged panels 506, 508, and 512.

Preferably, the hinged panels 502-512 are each sized according to an interior surface of a container, although the panels can be of other sizes. Before or after use, the liner sheet 500 can be unfolded and stored flat. Optionally, the liner sheet 500 can be folded along additional hinges (such as those indicated by dashed lines 532, 534, and 536) for storage. These additional hinges define hinged sub-panels.

As shown, optical fibers in the hinged panels 502-512 (such as those shown at 538, 540, and 542) can be connected together in series by optical jumpers (such as those shown at 544 and 546). A single set of optical connectors 548 can be used to connect the liner sheet 500 to a detector circuit or other panels. Alternatively, additional optical connectors (not shown) can be connected to ones or groups of the optical fibers. The liner sheet 500 has six panels 502-512 to monitor the six interior surfaces of a rectangular container. Other numbers and shapes of panels are acceptable, depending on the interior geometry of a container, the number of surfaces to be monitored, and the portion(s) of these surfaces to be monitored. It is, of course, acceptable to monitor fewer than all the interior surfaces of a container or less than the entire area of any particular surface.

Figure 6:
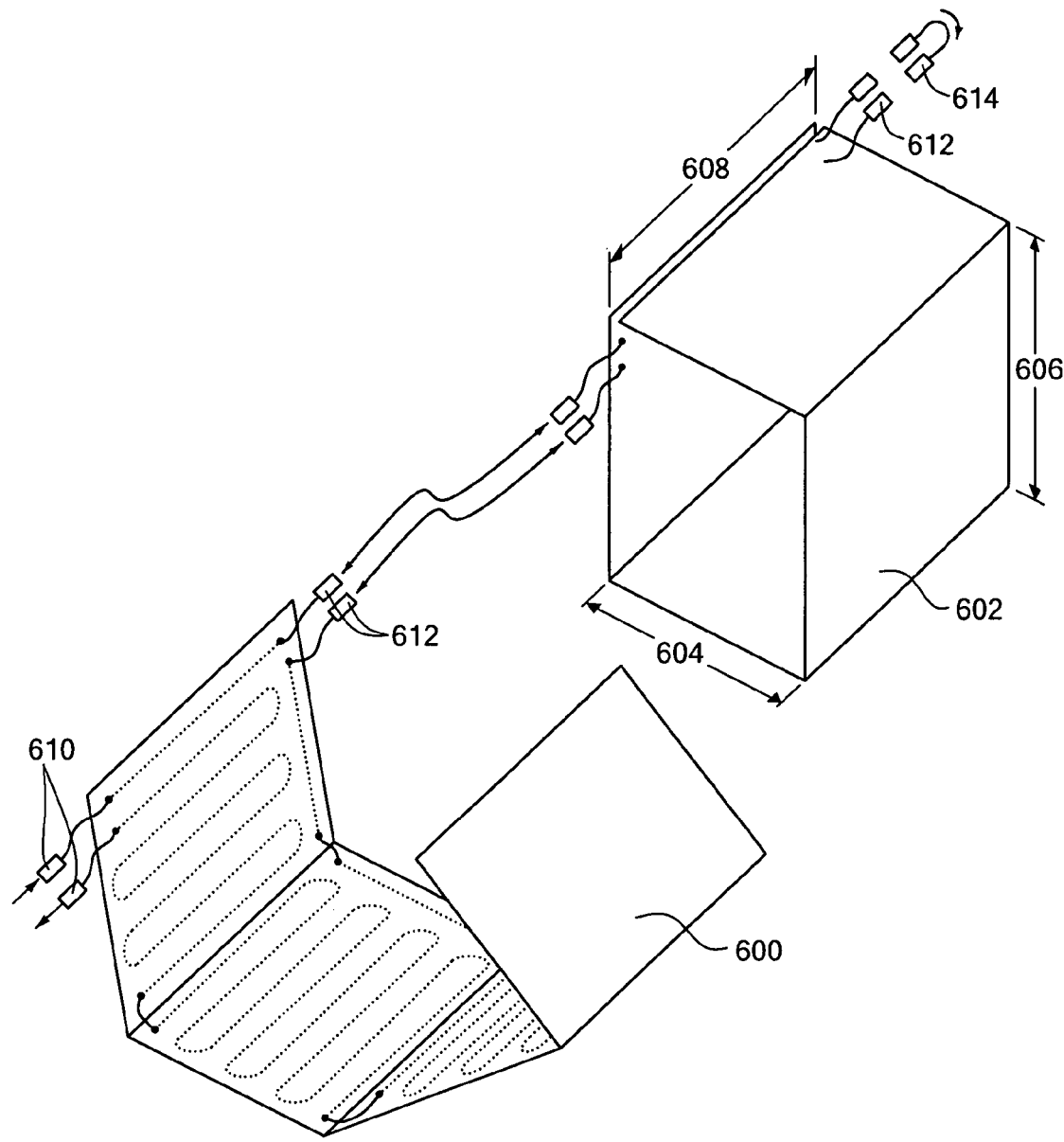
FIG. 6 is a perspective view of two modular liner units, according to another embodiment of the present invention.

As noted, ISO standard containers are available in various lengths. Many of these lengths are multiples of 10 or 20 feet. To avoid stocking liner sheets for each of these container lengths, an alternative embodiment, illustrated in FIG. 6, provides modular liner units, such as those shown at 600 and 602. The modular liner units 600-602 can include four (or another number of) hinged panels, as described above. Preferably, each modular liner unit 600-602 has a width 604 and a height 606 that corresponds to a dimension of a typical container. The length 608 of the modular units is chosen such that a whole number of modular units, placed end to end, can line any of several different size containers. For example, the length can be 9.8 feet or 19.8 feet. Such modular units can be easier to install than a single liner sheet (as shown in FIG. 5), because the modular units are smaller than a single liner sheet.

Each modular liner unit 600-602 preferably includes two sets of optical connectors 610 and 612, by which it can be connected to other modular units or to a detector circuit. A "loop back" optical jumper 614 completes the optical path by connecting to the optical connectors 612 of the last modular unit 602.

Figure 4:
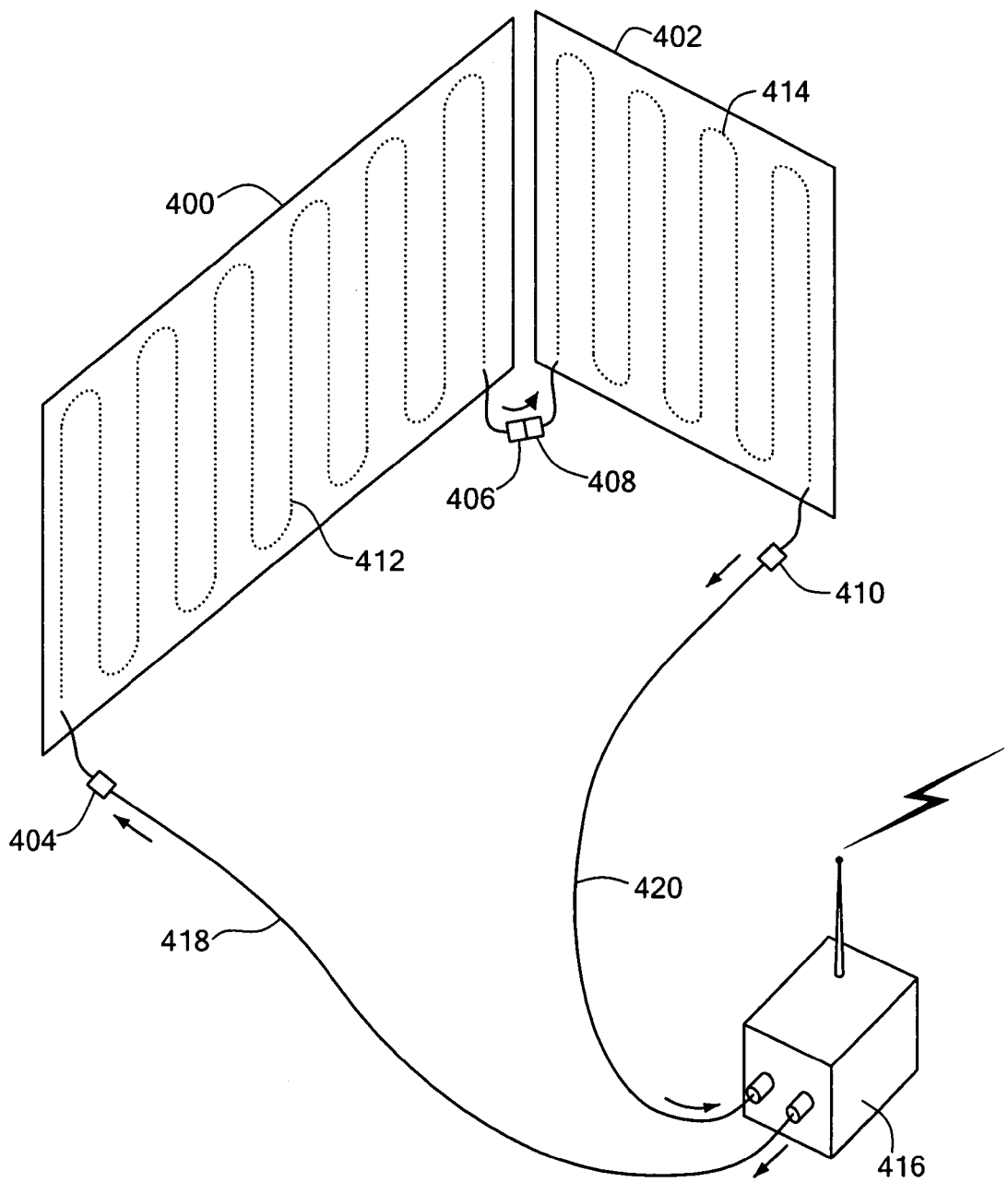
FIG. 4 is a perspective view of two liner sheets connected together, according to another embodiment of the present invention.
Figure 26:
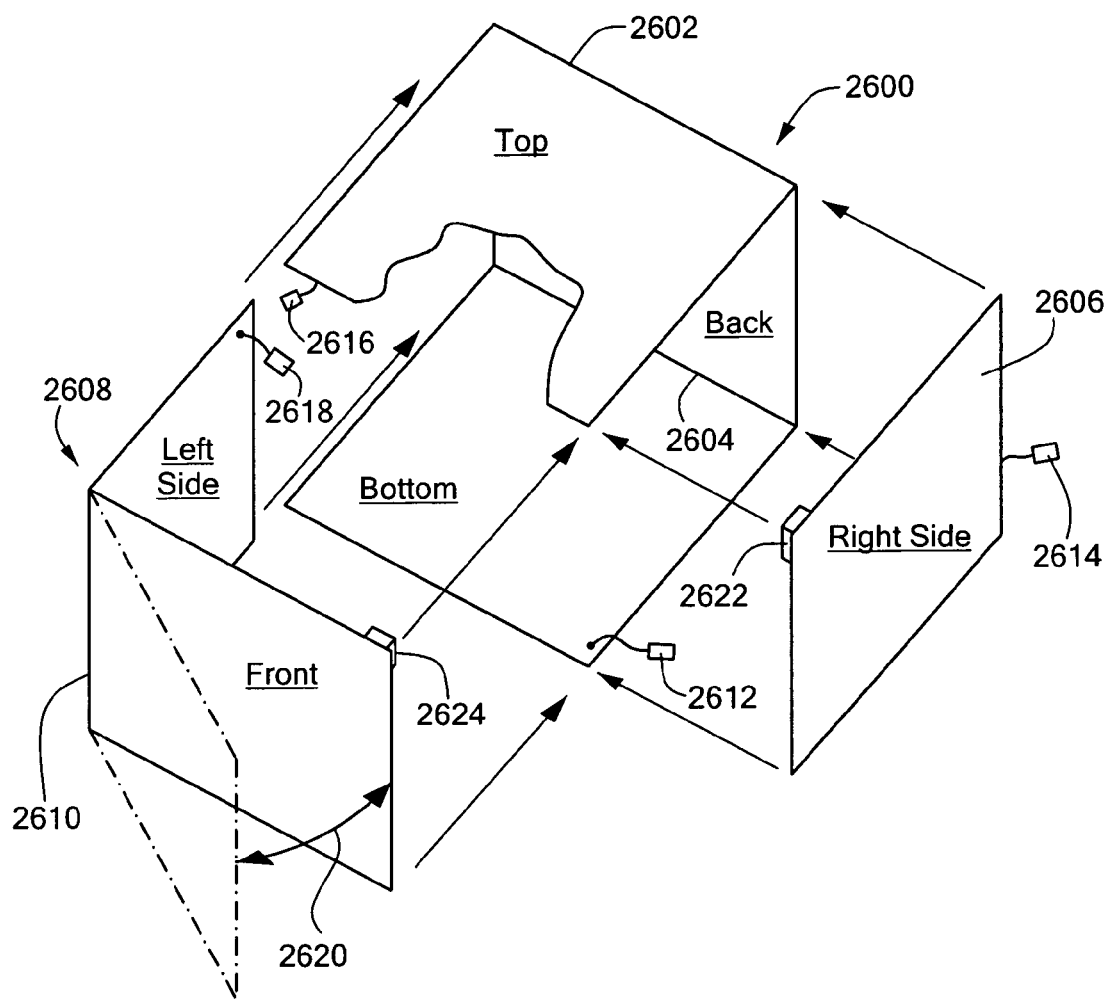
FIG. 26 is an exploded perspective view of a set of liner sheets, according to another embodiment of the present invention.

As noted with respect to FIG. 4, several liner sheets can be connected together to monitor several surfaces or to monitor a large area. Another such embodiment is shown in FIG. 26. In this embodiment, three liner sheets are interconnected to monitor the six interior surfaces of a container. One liner sheet 2600 is folded along two lines 2602 and 2604 to form a U-shaped structure that lines the top, back and bottom of the container. Another liner sheet 2606 lines the right side of the container. A third liner sheet 2608 is folded along a line 2610 to form an L-shaped structure that lines the left side and front of the container.

Optical fibers (not shown) in the first and second liner sheets 2600 and 2606 are interconnected by optical connectors 2612 and 2614. Similarly, optical fibers in the first and third liner sheets 2600 and 2608 are interconnected by optical connectors 2616 and 2618. Optical "extension cords" (not shown) can be used, if necessary.

The fold along line 2610 forms a hinge, so the front portion of the third liner sheet 2608 can pivot about the hinge, as shown by arrow 2620. The front portion of the third liner sheet 2608 therefore acts as a door. The door is opened to load or unload cargo into or out of the container. Once the cargo is loaded or unloaded and the front portion of the third liner sheet 2608 is closed, the door(s) of the container can be closed.

Figure 27:
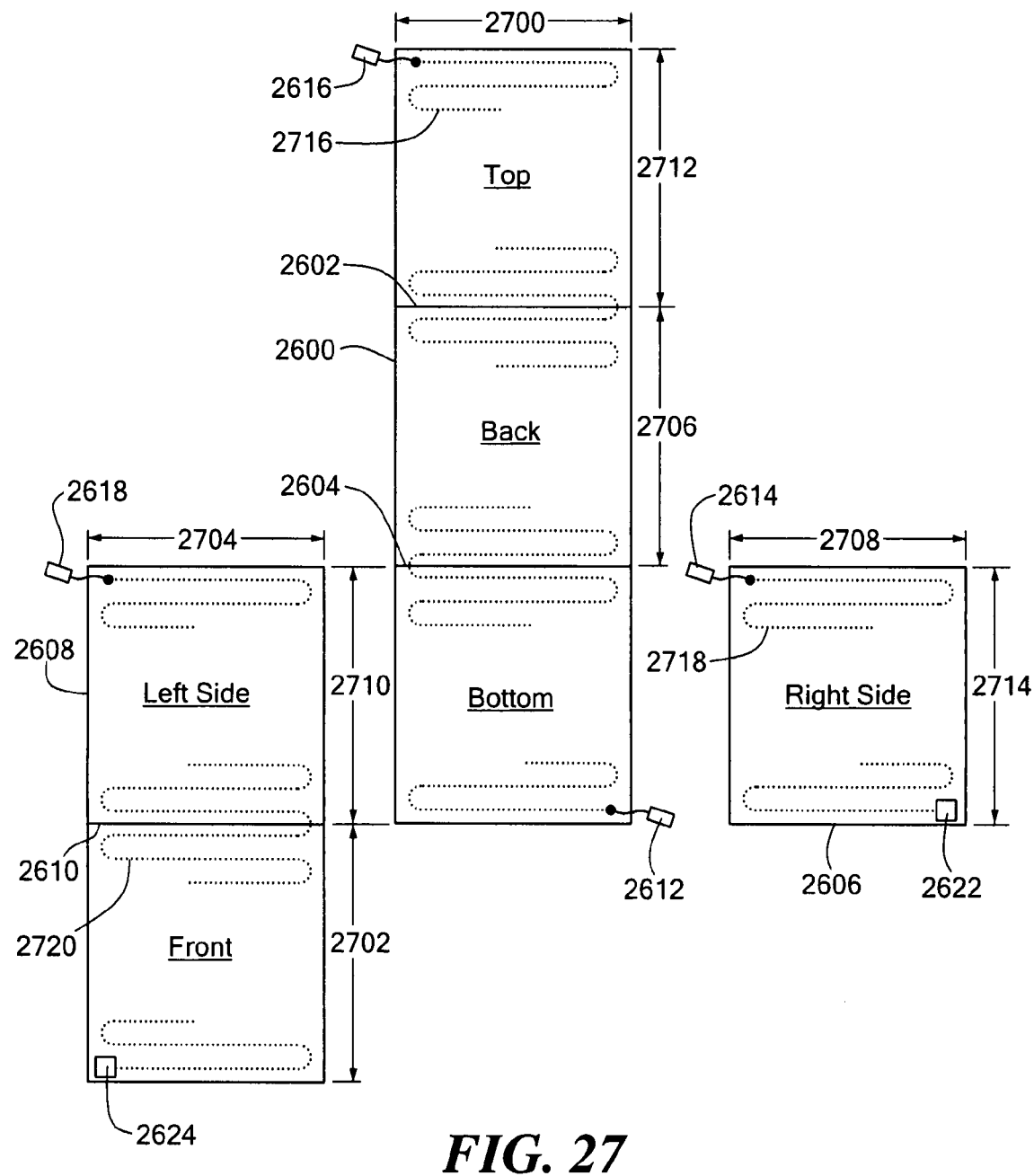
FIG. 27 is a plan view of the liner sheets of FIG. 26 laid flat.

The first, second and third liner sheets 2600, 2606 and 2608 are shown unfolded, i.e. laid out flat, in FIG. 27. The optical fibers are indicated by dotted lines 2716, 2718 and 2720. The dimensions of the liner sheets 2600, 2606 and 2608 can be selected according to the size of the container in which the liner sheets are to be used. For example, if the liner sheets are to be used in a 10 ft. long by 10 ft. wide by 10 ft. high container, each dimension is about 10 ft. or slightly less to accommodate installing the liner sheets in the container. For example, dimensions 2700 and 2702 are each slightly less than 10 ft., according to the width of the container; dimensions 2704, 2706 and 2708 are each slightly less than 10 ft., according to the height of the container; and dimensions 2710, 2712 and 2714 are each slightly less than 10 ft., according to the length of the container.

If the liners sheets 2600, 2606 and 2608 are to be used in a 20 ft. or 40 ft. long container, dimensions 2710, 2712 and 2714 are increased accordingly. Similarly, if the liner sheets are to be used in a shorter, taller, wider or narrower container, the appropriate dimensions are adjusted accordingly.

Figure 29:
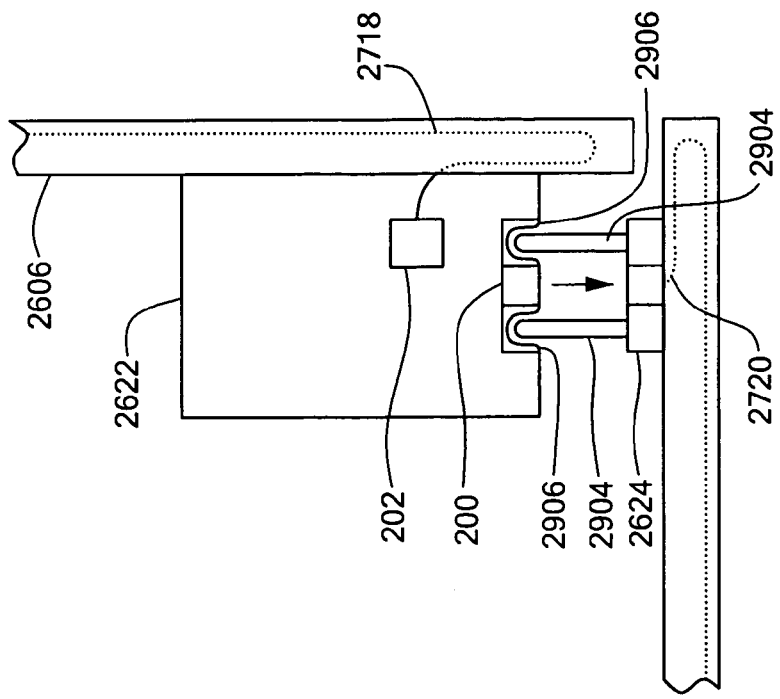
FIG. 29 is an enlarged view of a portion of the top view of FIG. 28.
Figure 28:
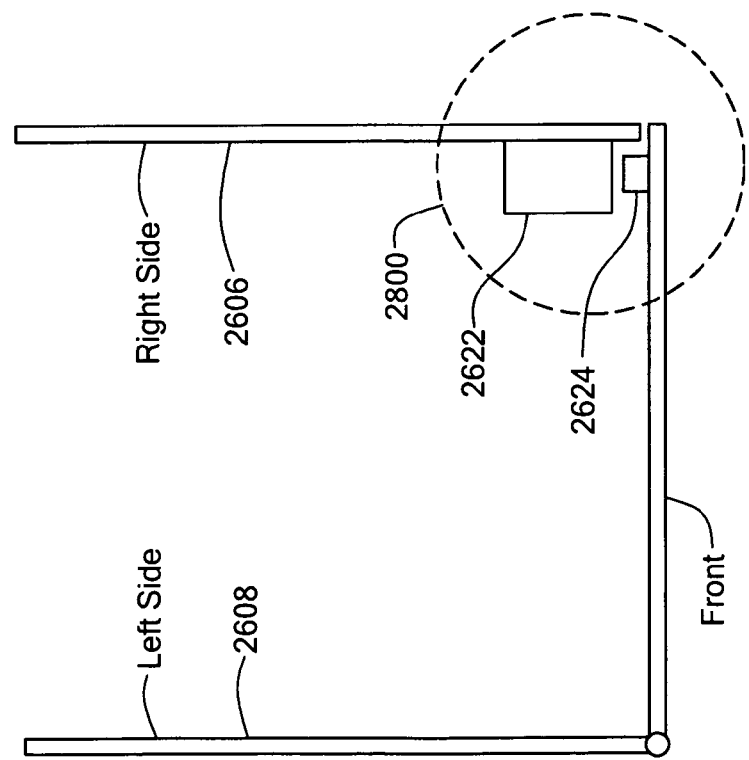
FIG. 28 is a top view of a portion of the liner sheets of FIG. 26.

Returning to FIG. 26, the detector circuit 204 discussed above with reference to FIG. 2 is enclosed in a housing 2622 attached near an upper corner of the right liner sheet 2606. A second housing 2624 is mounted near an upper corner of the front portion (i.e. door) of the liner sheet 2608. FIG. 28 is a top view of the right liner sheet 2606, the front portion of the liner sheet 2608 and the housings 2622 and 2624 mounted thereto. FIG. 29 is an enlarged view of a portion 2800 of FIG. 28. A light detector 202 is coupled to the optical fiber 2718 in the right side liner sheet 2606. A light source 200 in the housing 2622 optically couples with an end of the optical fiber 2720 in the front portion of liner sheet 2608.

When the front portion of liner sheet 2608 (i.e. the door) is closed, the housing 2624 attached thereto aligns the optical fiber 2720 in the front portion of the liner sheet with the light source 200 in the housing 2622 attached to the right side liner sheet 2606, thereby optically coupling the light source 200 with the optical fiber 2720. Alignment pins 2904 projecting from the housing 2624 mate with recesses 2906 in the other housing 2622 to facilitate aligning the light source 200 and the optical fiber 2720. Alternatively, rather than including the alignment pins 2904, the housing 2624 can be cone shaped and configured to mate with a cone shaped recess in the other housing 2622.

Of course, the functions of the light source 200 and the light detector 202 can be interchanged. That is, the light source can be coupled to the optical fiber 2718 in the right side liner sheet 2606, and the light detector can be coupled to the optical fiber 2720 in the front portion of the liner sheet 2608. Other configurations are also possible, as would be evident to those of ordinary skill in the art.

Figure 30:
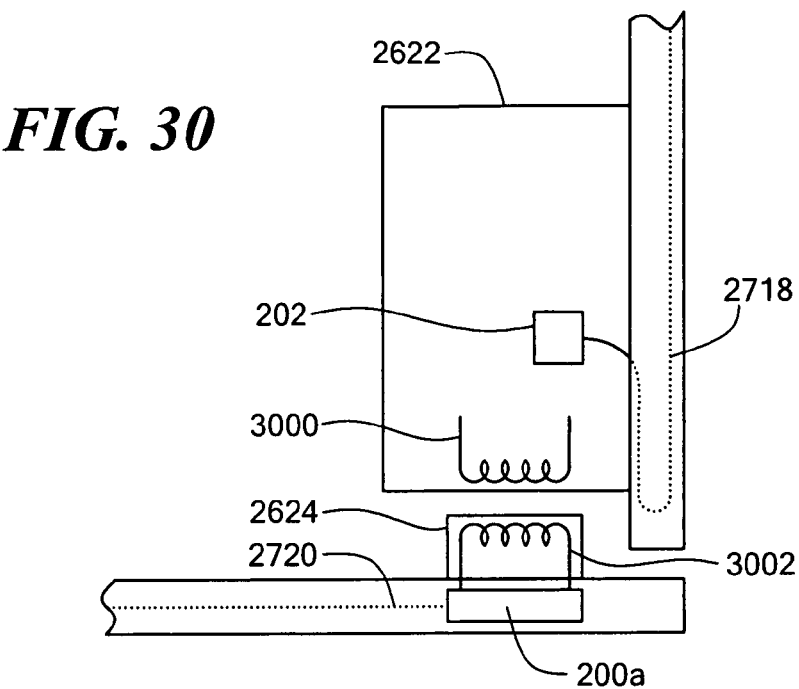
FIG. 30 is a diagram of an alternative embodiment to the one show in FIG. 29.

Alternatively, rather than optically coupling the circuits in the two housings 2622 and 2624, the circuits can be electromagnetically coupled. For example, as shown in FIG. 30, the housing 2622 includes a coil 3000 that electromagnetically couples with a second coil 3002 in the other housing 2624 when the front portion (i.e. door) of the liner sheet 2608 is closed. The first coil 3000 is provided with an AC signal. Due to the proximity of the two coils 3000 and 3002, an AC signal is induced in the second coil 3002, which is connected to a circuit 200a. The circuit 200a rectifies the received AC signal and drives a light source coupled to the optical fiber 2720.

Figure 7:
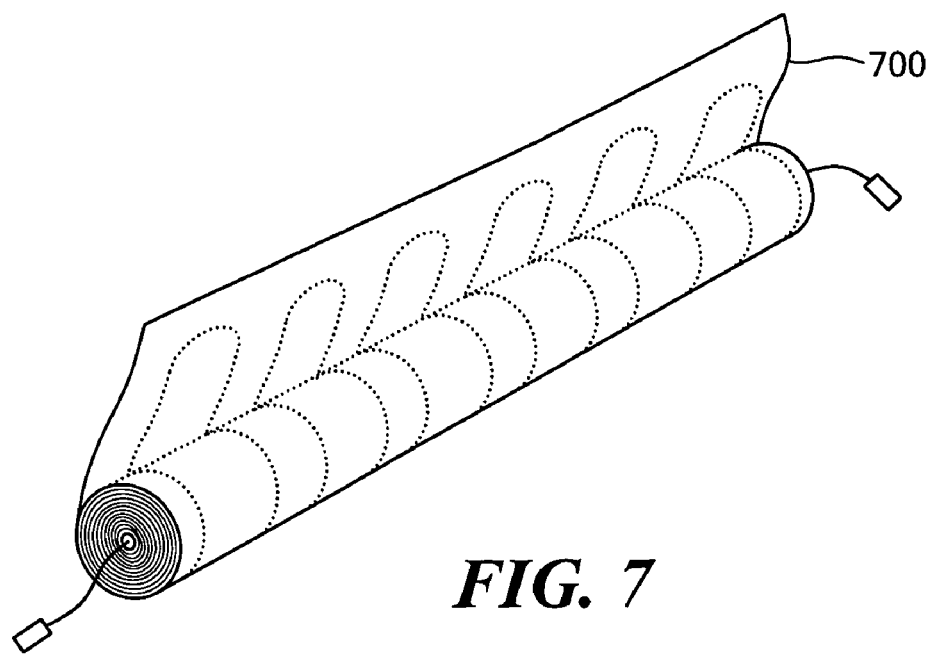
FIG. 7 is a perspective view of a flexible, rollable liner sheet, according to another embodiment of the present invention.

A liner sheet or panel according to the present invention can be implemented in various forms. For example, rigid, semi-rigid and flexible panels have been described above, with respect to FIGS. 1 and 5. Panels can be manufactured from a variety of materials including cardboard, foamboard, plastic, fiberglass or composite materials or woven or non-woven fabric material. The optical fiber can be embedded in the panel or placed on a panel surface and covered with a protective coating or sheet. FIG. 7 illustrates another embodiment, in which a liner sheet 700 is made of a flexible, rollable material. The liner sheet 700 can be unrolled prior to installation in a container and later re-rolled for storage. Such a flexible liner sheet can be attached and connected as described above, with respect to rigid panels.

Figure 8:
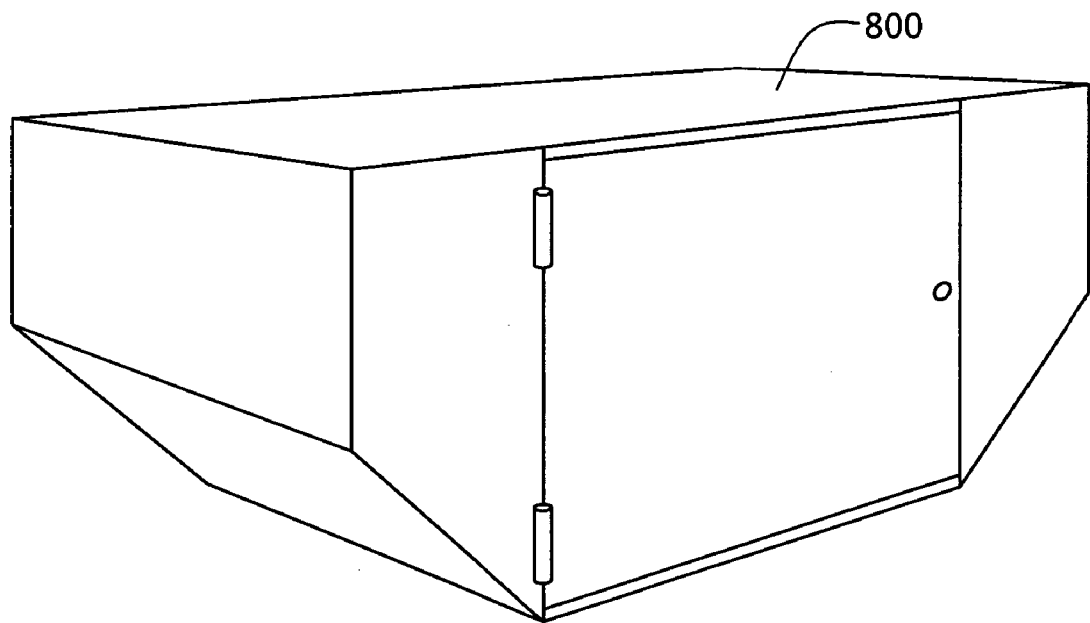
FIG. 8 is a perspective view of an aircraft container, in which an embodiment of the present invention can be advantageously practiced.

Although the present invention has thus far been described for use in ISO and other similar shipping containers, other embodiments can be used in other types of shipping containers boxes. For example, FIG. 8 illustrates an LD3 800 container typically used on some aircraft. Embodiments of the present invention can be sized and shaped for use in LD3, LD3 half size, LD2 or other size and shape aircraft containers or containers used on other types of transport vehicles or craft.

Yet other embodiments of the present invention can be used in shipping boxes, such as those used to ship goods via a parcel service or for shipping large bundles of currency by an armored truck service. In the case of currency shipment, the currency packets can be independently monitored as to packaging integrity as well as location monitoring, by enclosing the packets in a box or other container having a continuous fiber path in accordance with the invention. Similar packaging can be employed for containing and shipping other small volume high value cargo.

Figure 9:
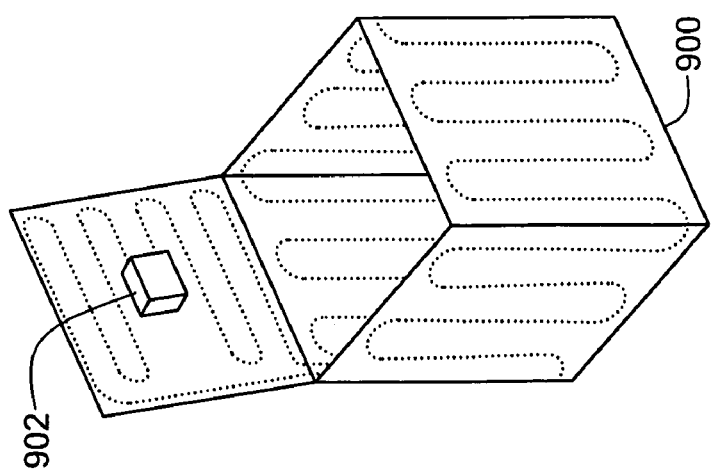
FIG. 9 is a perspective view of a box liner, according to another embodiment of the present invention.

FIG. 9 illustrates a liner sheet 900 that can be placed inside a box. The liner 900 can include a control circuit 902 that includes the detector circuit 204 (FIG. 2) and the associated other circuits described above. Such a liner sheet need not necessarily be attached to the interior surfaces of a box. The liner sheet 900 can be merely placed inside the box. Optionally, the control circuit 902 can include a data recorder to record, for example, a time and location of a detected breach. The control unit 902 can also include a transmitter, by which it can notify a central location, such as a shipper's operations center of its location and its breach and radiation status.

Furthermore, as noted, embodiments of the present invention are not limited to rectangular containers, nor are they limited to containers with flat surfaces. For example, liner sheets can be bent, curved, shaped or stretched to conform to a surface, such as a curved surface, of a container.

Figure 10:
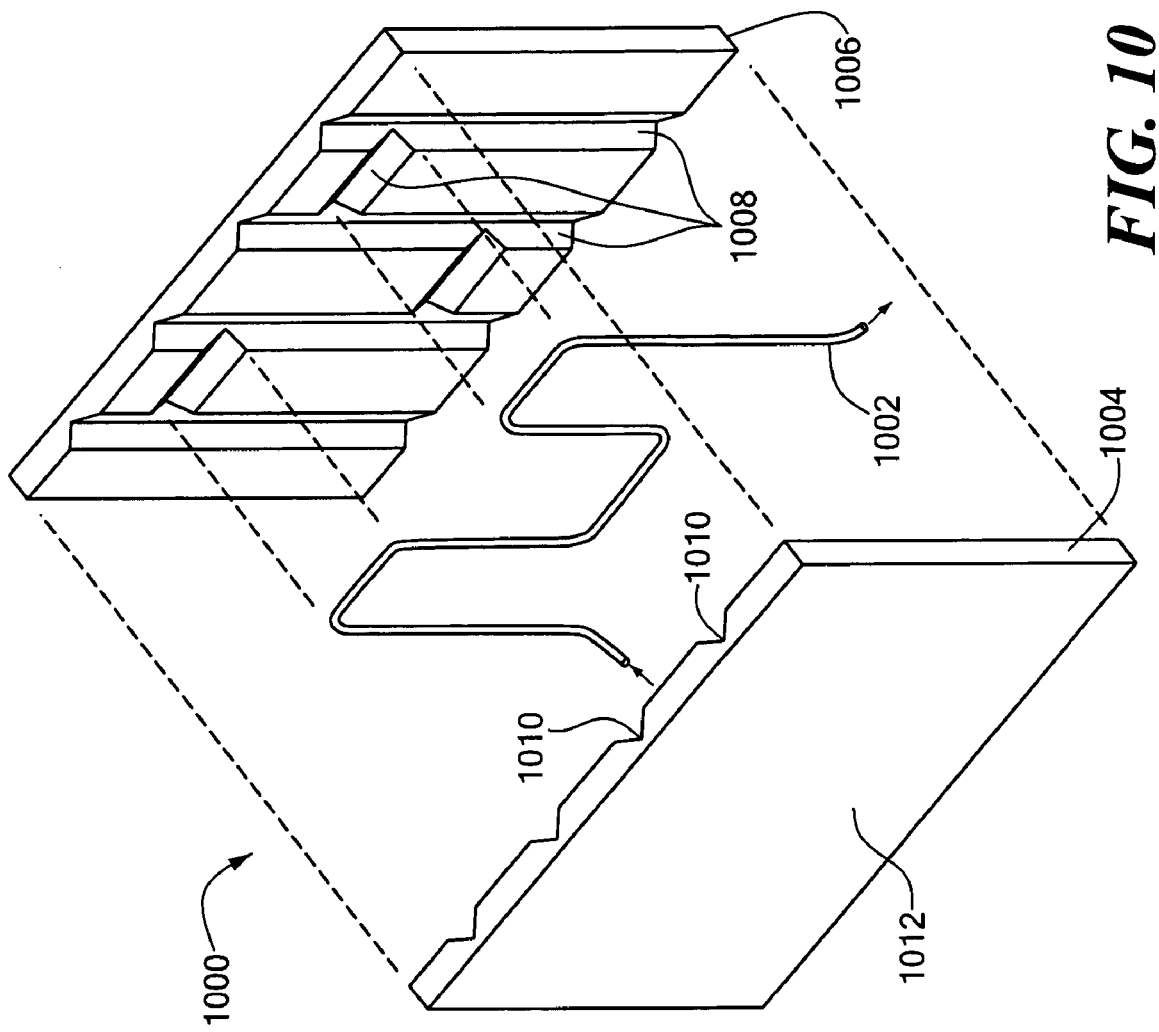
FIG. 10 is an exploded view of a rigid panel, according to one embodiment of the present invention.

As noted, a liner sheet according to the present invention can be implemented in various forms. FIG. 10 is an exploded view of one embodiment of a panel 1000 having an optical fiber 1002 sandwiched between two layers 1004 and 1006. One of the layers 1004 or 1006 can be a substrate, upon which the other layer is overlaid. A groove, such as indicated at 1008, is formed in one of the layers 1006, such as by scoring, cutting, milling, stamping or molding. Optionally, a corresponding groove 1010 is formed in the other layer 1004. The optical fiber 1002 is inserted in the groove(s) 1008(-1010), and the two layers 1004-1006 are joined. Alternatively, the optical fiber can be molded into a panel or sandwiched between two layers while the layers are soft, such as before they are fully cured. Optionally, a surface (for example surface 1012) of one of the layers can be made of a stronger material, or it can be treated to become stronger, than the rest of the panel 1000. Suitable materials for the surfaces include wood, rubber, carpet and industrial fabric or carpet. When the panel 1000 is installed in a container, this surface 1012 can be made to face the interior of the container. Such a surface can better resist impact, and thus accidental damage, from cargo and equipment as the cargo is being loaded or unloaded.

Figure 11:
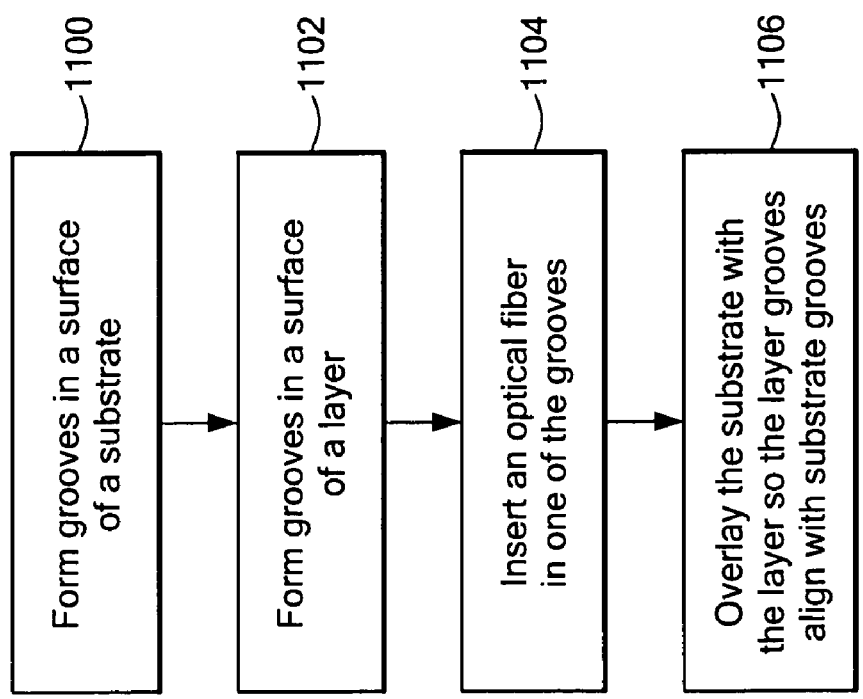
FIG. 11 is a simplified flowchart illustrating a process for fabricating a liner sheet, such as the one illustrated in FIG. 10.

FIG. 11 illustrates a process for fabricating a panel, such as the panel 1000 described above. At 1100, one or more grooves are formed in a substrate. At 1102, one or more grooves are formed in a layer that is to be overlaid on the substrate. At 1104, an optical fiber is inserted in one of the grooves. At 1106, the substrate is overlaid with the layer.

Figure 12:
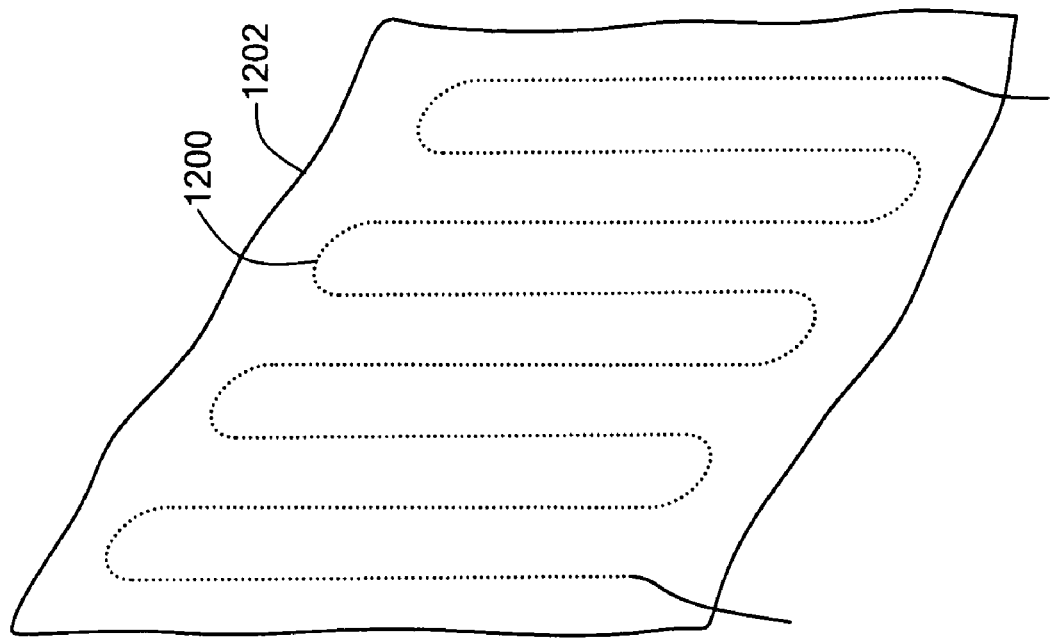
FIG. 12 is a perspective view of a fabric embodiment of a liner sheet, according to one embodiment of the present invention.
Figure 13:
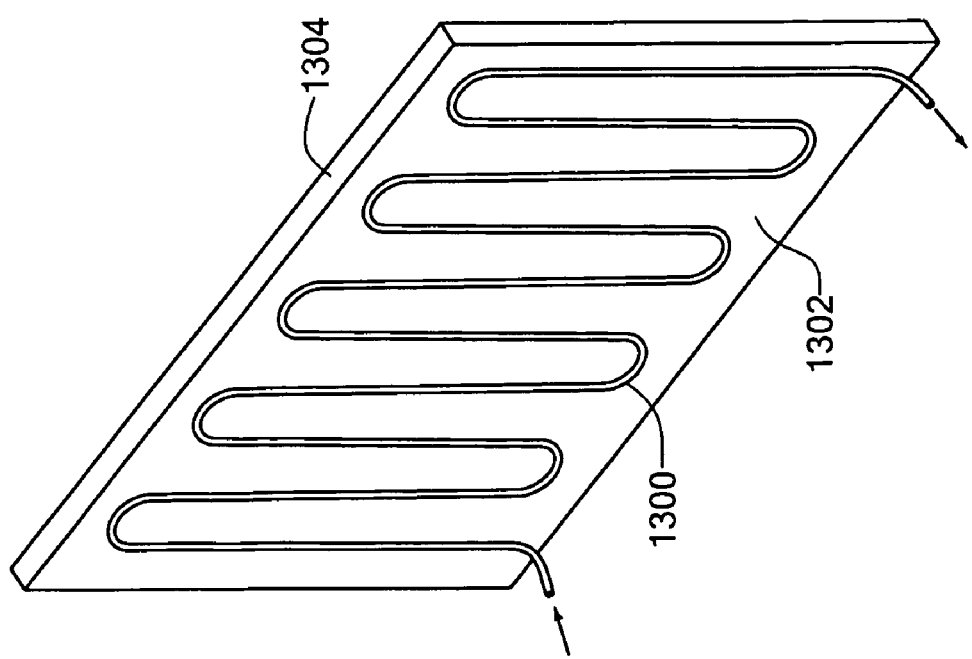
FIG. 13 is a perspective view of a liner sheet panel with an optical fiber attached to its surface, according to one embodiment of the present invention.

Thus far, panels with optical fibers embedded within the panels have been described. Alternatively, as illustrated in FIG. 12, an optical fiber 1200 can be woven into a woven or non-woven (such as spun) fabric 1202. In addition, an optical fiber can be woven or threaded through a blanket, carpet or similar material. As noted above, and as illustrated in FIG. 13, an optical fiber 1300 can be attached to a surface 1302 of a flexible or rigid panel 1304.

Figure 14:
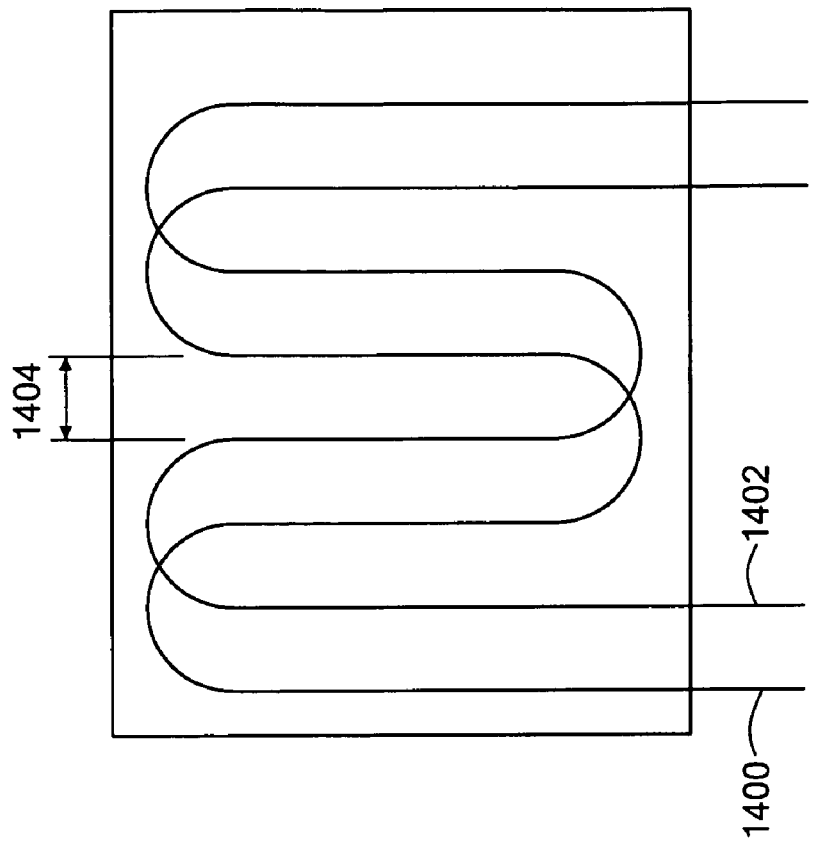
FIGS. 14 and 15 are plan views of liner sheets, each having more than one optical fiber, according to two embodiments of the present invention.
Figure 15:
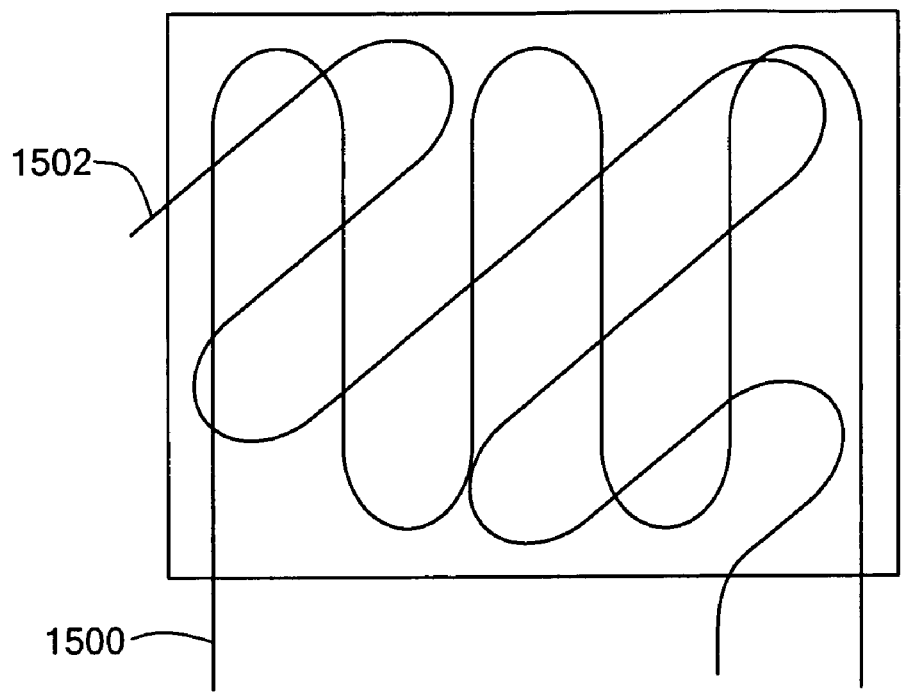

As noted, a pitch or spacing 108 between adjacent portions of the optical fiber 106 (FIG. 1) can be selected according to the minimum size breach in the container 100 that is to be detected. In the embodiment shown in FIG. 1, the spacing 108 is approximately equal to twice the radius of bend 116 in the optical fiber 106. However, many optical fibers have minimum practical bend radii. If such an optical fiber is bent with a radius less than this minimum, loss of light transmission through the bent portion of the optical fiber can occur. As shown in FIG. 14, to avoid such loss in situations where a pitch less than twice the minimum bend radius is desired, two or more optical fibers 1400 and 1402 can be can be interlaced. In such an embodiment, if N optical fibers are used and each optical fiber is bent at its minimum radius, the spacing (e.g. 1404) between the optical fibers can be approximately 1/N the minimum spacing of a single optical fiber. The optical fibers can be approximately parallel, as shown in FIG. 14, or they can be non-parallel. For example, as shown in FIG. 15, the optical fibers 1500 and 1502 can be disposed at an angle with respect to each other. Alternatively (not shown), two liner sheets can be used, one on top of the other, to line a single surface of a container. The optical fibers of these two liner sheets can, for example, be oriented at an angle to each other, offset from each other or otherwise to provide a tighter pitch than can be provided by one liner sheet alone or to provide redundant protection, such as for especially sensitive cargo.

Figure 16:
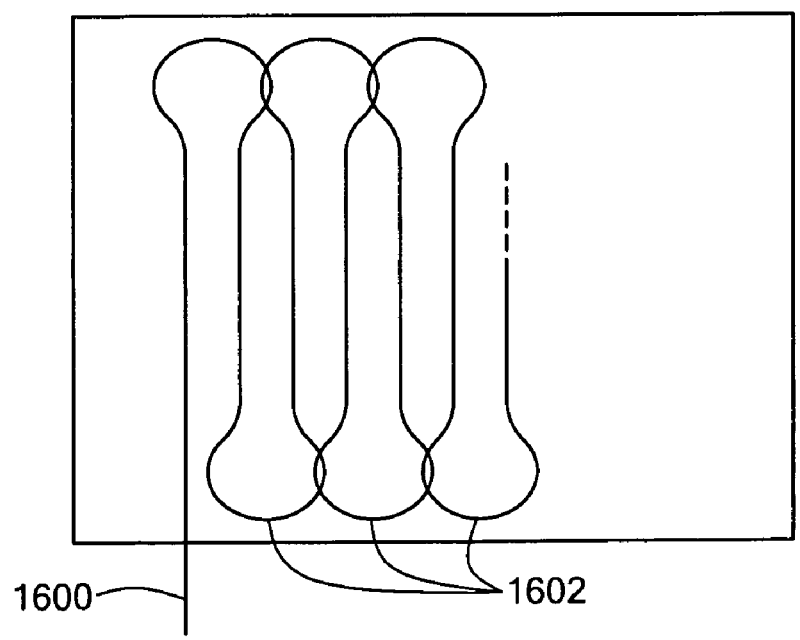
FIGS. 16, 17, 18 and 19 are plan views of liner sheets, each having one optical fiber, according to four embodiments of the present invention.
Figure 17:
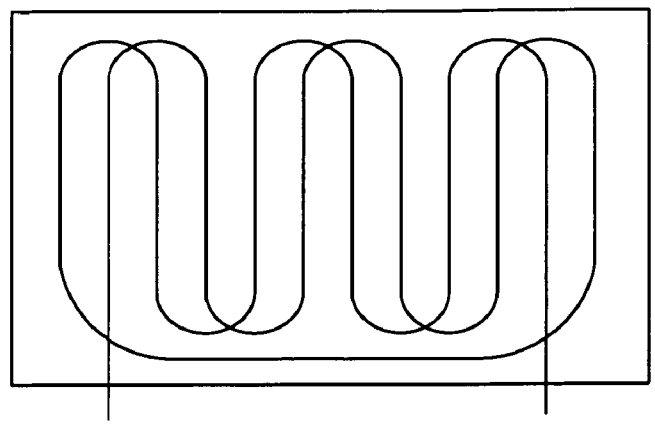
Figure 18:
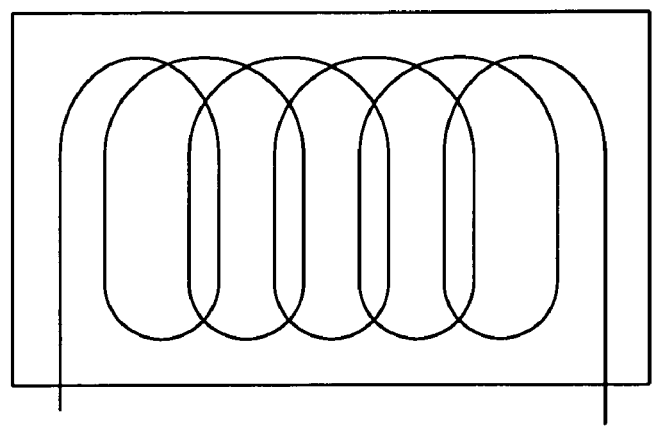
Figure 19:
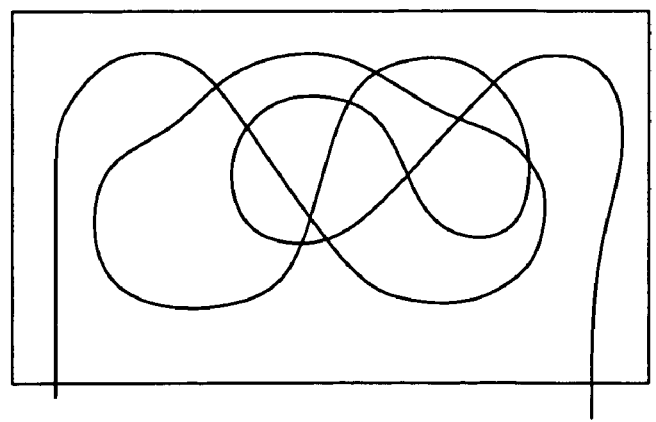

In another embodiment shown in FIG. 16, a single optical fiber 1600 can be configured so loops, such as those shown at 1602, at the ends of the optical fiber segments each occupy more than 180° of curvature and, thus, provide a reduced spacing. Other configurations of a single optical fiber providing a reduced spacing are shown in FIGS. 17, 18 and 19.

Figure 20:
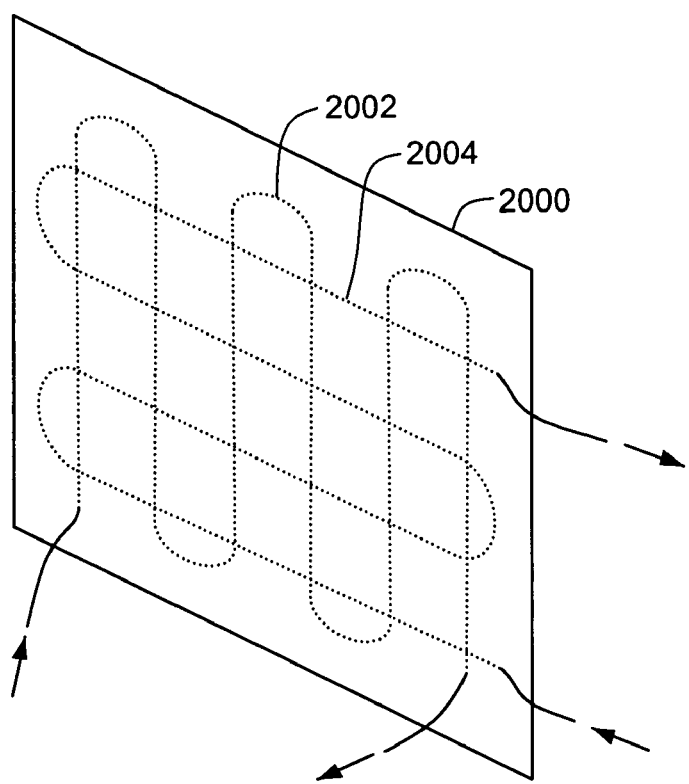
FIG. 20 is a perspective view of a liner sheet having more than one optical fiber, according to one embodiment of the present invention.
Figure 21:
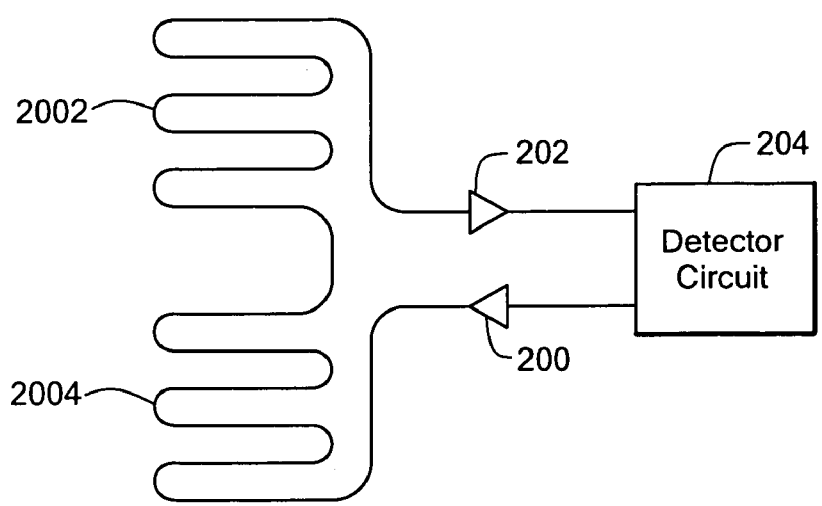
FIG. 21 is a simplified schematic diagram of the liner sheet of FIG. 14 and associated circuitry, according to one embodiment of the present invention.

As noted, more than one optical fiber can be included in each liner sheet. FIG. 20 shows a liner sheet 2000 with two optical fibers 2002 and 2004. As shown in FIG. 21, the optical fibers 2002, 2004 can be connected to each other in series, and the respective optical fibers can be connected to a single light source 200 and a single light detector 202. Alternatively (not shown), the optical fibers 2002, 2004 can be connected to each other in parallel, and the optical fibers can be connected to a single light source and a single light detector.

Figure 22:
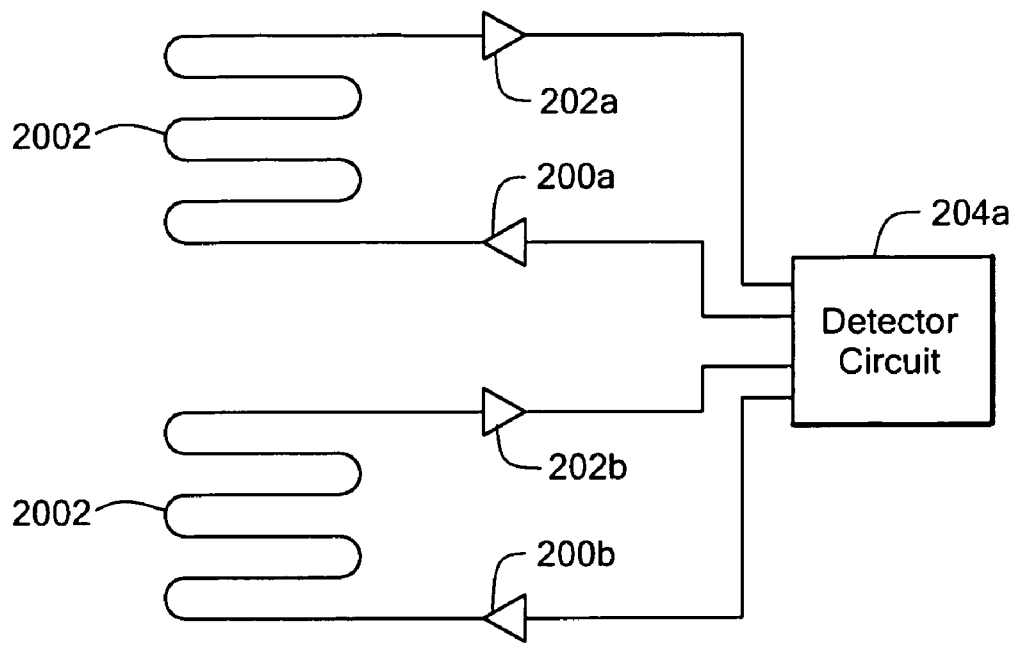
FIG. 22 is a simplified schematic diagram of the liner sheet of FIG. 14 and associated circuitry, according to another embodiment of the present invention.

In an alternative embodiment shown in FIG. 22, each optical fiber 2002, 2004 can be connected to its own light source 200a and 200b (respectively) and its own light detector 202a and 202b (respectively). In this case, signals from the optical fibers 2002, 2004 can be processes in series or in parallel by a detector circuit 204a.

In a further embodiment, multiple panels each having one or more continuous optical fiber paths can be overlayed in an offset manner to reduce the pitch between adjacent portions of the optical fiber.

A parallel connection of the optical fibers 2002, 2004, or a parallel processing of the signals from the optical fibers, would tolerate some breakage of the optical fibers without triggering an alarm. Such breakage might be expected, due to rough handling that the panels might undergo as containers are loaded and unloaded. The amount of light transmitted by several parallel optical fibers depends on the number of the optical fibers that remain intact. Once a container is loaded, the system could sense which fibers are intact and ignore damaged or severed fibers. Alternatively, the system could sense the amount of light being transmitted and set that amount as a reference amount. Later, in transit, if the amount of transmitted light fell below the reference amount, the system could signal a breach or shift in cargo, as discussed above. Of course, not all the optical fibers need be used at one time. Some of the optical fibers can be left as spares and used if primary optical fibers are damaged.

Figure 23:
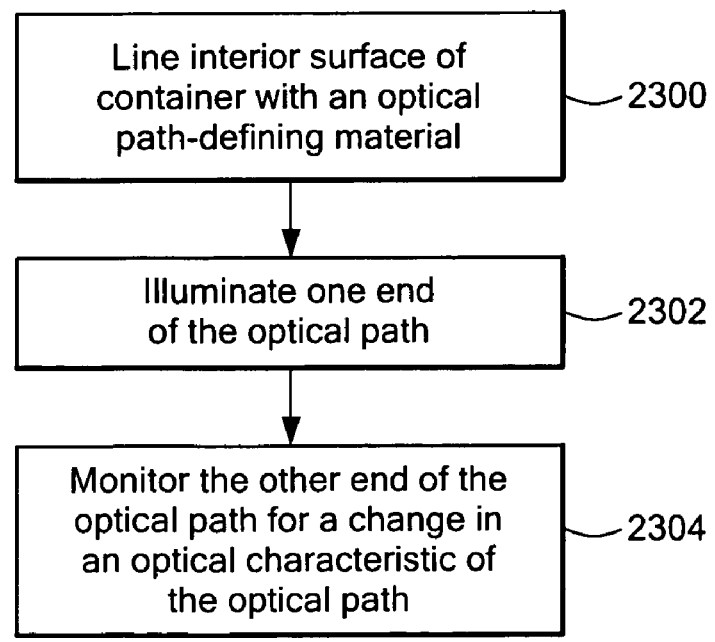
FIG. 23 is a simplified flowchart of a method of monitoring a container, according to one embodiment of the present invention.

Any of the above-described liner sheets or variations thereon can be used to monitor a container. FIG. 23 illustrates a process for monitoring a container. At 2300, at least one interior surface, or a portion thereof, is lined with an optical path-defining material. At 2302, one end of the optical path is illuminated. At 2304, the other end of the optical path is monitored for a change in an optical characteristic of the optical path.

Figure 31:
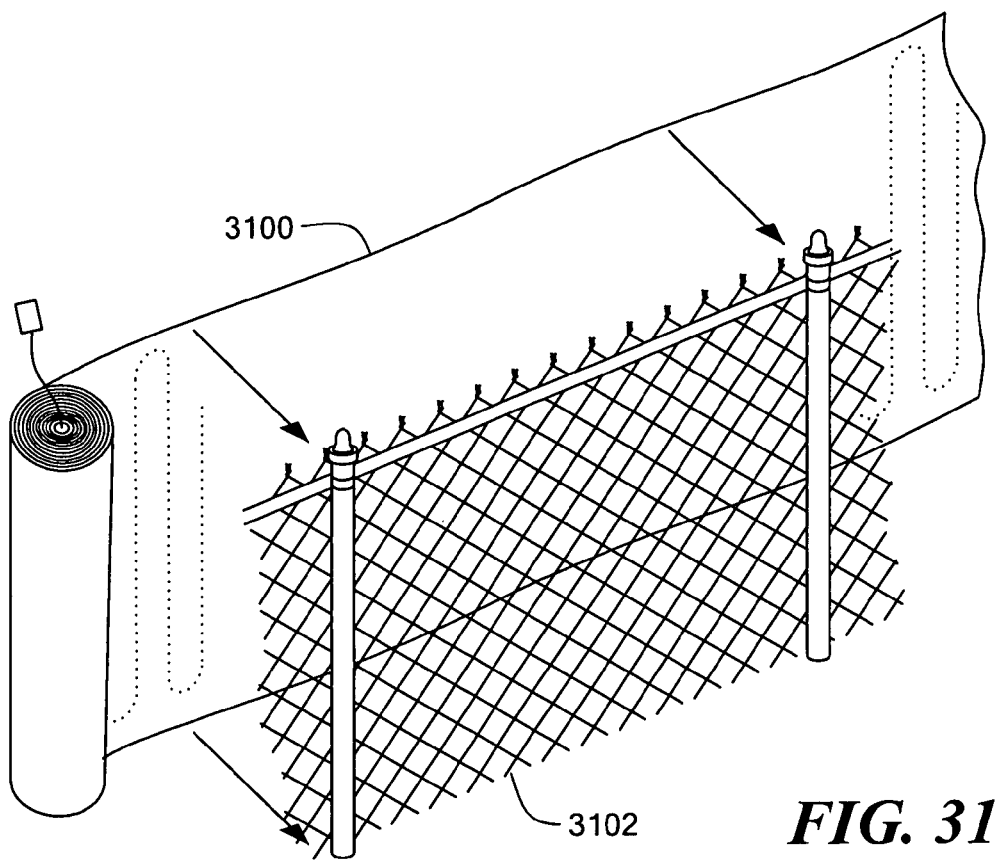
FIG. 31 is an exploded perspective view of a liner sheet attached to a fence, according to another embodiment of the present invention.

The invention has been described in relation to closed (i.e. entirely surrounded) containers, rooms and the like, however embodiments are also applicable to protecting open areas, such as yards. For example, as shown in FIG. 31, a liner panel 3100 can be attached to a fence 3102, such as a chain link fence, to monitor the fence for breaches thereof or radiation near the fence. For example, the flexible liner sheet described above with reference to FIG. 7 can be attached to the fence by any suitable fastener. For example, the liner sheet 3100 can include eyelets, and the liner sheet can be attached to the fence by screws, twisted wires or the like. Alternatively, one or more flexible, rigid or semi-rigid panels can be attached to the fence and interconnected in series, as discussed above. A relatively long liner sheet attached to a fence integrates nuclear radiation, as discussed above. Therefore, such a liner sheet is sensitive to relatively low-level radiation in its vicinity.

In an alternative implementation, a thin electrical wire or path can be utilized rather than the optical fiber described above. For example, a thin electrical wire can be arranged in a zigzag path across the area of a panel or woven into a fabric to provide breakage detection similar to that of the fiber optic embodiment described above. An electrical signal or energy source and electrical detector detects a break in the conductive path and sends an alarm in the same fashion as described in the fiber optic embodiment. For some purposes, such as for redundancy, one or more panels having an electric wire path can be employed with one or more panels having an optical fiber path.

While the invention has been described with reference to a preferred embodiment, those skilled in the art will understand and appreciate that variations can be made while still remaining within the spirit and scope of the present invention, as described in the appended claims. For example, although some embodiments were described in relation to shipping containers used to transport cargo, these containers can also be used to store cargo in warehouses, yards and the like, as well as during loading and unloading of the containers at a loading dock. Some embodiments were described in relation to shipping containers used on ships, etc. These and other embodiments can also be used with shipping boxes and other types of containers that may be transported by plane, truck, railcar, bus car or other means. The invention can also be used to detect tampering with, or a break into or out of, a room of a structure, such as an office, vault or prison cell. The term "container" in the claims is, therefore, to be construed broadly to include various types of shipping containers and boxes, as well as rooms and open areas, such as yards, that are surrounded by fences or the like. Functions described above, such as differential amplifiers, comparators, triggers and alarms, can be implemented with discrete circuits, integrated circuits and/or processors executing software or firmware stored in memory. In addition, the optical paths have been described as being created using optical fibers. Other mechanisms can, however, be used to create optical paths. For example, hollow tubes and mirrors or combinations of technologies can be used to define optical paths through panels.

What is claimed is:

1. A radiation detection system for a multisided container comprising:
    a plurality of liner panels each sized to line an interior wall of a respective side of the container;
    each of the liner panels having an optical fiber embedded therein and extending in a path across substantially the entire area of the panel, the optical fiber having a first end and a second end;
    the optical fiber being reactive to nuclear radiation impinging on the panel to cause an irreversible decrease in light-carrying capacity of the optical fiber;
    the ends of the optical fiber of the plurality of liner panels being interconnected to provide a continuous optical path through the plurality of liner panels;
    a light source optically coupled to one end of the optical fiber path of the interconnected liner panels for introducing light having a coded pattern of light;
    a light detector optically coupled to the other end of the optical path of the interconnected liner panels for receiving light from the optical path;
    a circuit connected to the light detector and operative to detect a change in the error rate in the coded pattern of the light in the optical fiber and in response to radiation impinging on the optical fiber to provide an indication thereof;
    wherein the circuit connected to the light detector is operative to:
    determine a profile of the error rate over time in response to radiation impinging on the optical fiber; and
    provide an output indication of a changed profile above a predetermined threshold.

2. The radiation detection system of claim 1 further including a memory storing one or more profiles of radiation sources;
    the circuit connected to the light detector including apparatus for comparing the profile of light received from the optical path with profiles stored in the memory and for providing an output indication identifying the specific radioactive material and source of the detected radiation.

3. The radiation detection system of claim 2 wherein the memory comprises a memory unit for storing data from various radioactive sources according to the half-life decay formula $N=N_o\exp(-\gamma t)$ which gives an identifying decay signature of the specific radioactive isotope.

4. The radiation detection system of claim 3 wherein the memory unit additionally stores data identifying the decay signature of any ensuing radioactive daughter isotopes created by the decay of the parent or original isotope.

5. The radiation detection system of claim 1 wherein the light source provides polarized light to one end of the optical fiber path; and the circuit connected to the light detector is operative to detect a change in the polarization of light received from the optical path representative of radiation impinging on the optical fiber.

6. The radiation detection system of claim 5 wherein the circuit connected to the light detector is operative to detect changes in the relative speed of orthogonally polarized components of polarized light received from the optical fiber, which changes are representative of radiation impinging on the optical fiber.

7. The system of claim 1 wherein the optical fiber extends in a serpentine path across substantially the entire area of the panel.

8. The system of claim 7 wherein spacing between adjacent portions of the optical fiber is of a smaller size than a breach that could compromise the security of the container.

9. The system of claim 8 wherein multiple liner panels are placed one on top of the other in an offset mariner to reduce the spacing between adjacent portions of the optical fiber.

10. The system of claim 7 wherein spacing between adjacent portions of the optical fiber is sufficiently small to cause breakage or degradation of the optical fiber in reaction to an attempted breach of the panel.

11. The system of claim 1 wherein each of the plurality of liner panels is rectangular.

12. The radiation detection system of claim 1 wherein the light source provides light having a wavelength that enhances the sensitivity of the optical fiber to the radiation-induced change in the predetermined characteristic of light in the optical fiber.

13. The radiation detection system of claim 1 wherein the liner panels are integral with the container sides.

14. The radiation detection system of claim 1 wherein the optical fiber includes one or more dopants which enhance sensitivity of the optical fiber to the radiation induced change in the predetermined characteristic of light in the optical fiber.

15. The radiation detection system of claim 1 wherein the container has insulated sides to trap heat from a nuclear source within the container, and including sensing apparatus for measuring temperature rise caused by the nuclear source.

16. The radiation detection system of claim 1 wherein the entire enclosed volumetric space of the container; and the surrounding volumetric mass of the optical fiber constitutes a radiation detection system which totally encapsulates radioactive material in the container.

17. The radiation detection system of claim 1 including a telecommunication interface operative to transmit a detection signal from the circuit that indicates an alarm condition to one or more monitoring stations.

* * * * *

UNITED STATES PATENT AND TRADEMARK OFFICE
CERTIFICATE OF CORRECTION

PATENT NO. : 7,332,728 B2 Page 1 of 1
APPLICATION NO. : 11/444160
DATED : February 19, 2008
INVENTOR(S) : Gilbert D. Beinhocker It is certified that error appears in the above-identified patent and that said Letters Patent is hereby corrected as shown below:

Column 27, claim 9, line 30, "mariner" should read --manner--.

Signed and Sealed this

Twenty-sixth Day of May, 2009

JOHN DOLL
*Acting Director of the United States Patent and Trademark Office*